United States Patent [19]

Kaufman et al.

[11] Patent Number: 5,142,484

[45] Date of Patent: * Aug. 25, 1992

[54] AN INTERACTIVE PATIENT ASSISTANCE DEVICE FOR STORING AND DISPENSING PRESCRIBED MEDICATION AND PHYSICAL DEVICE

[75] Inventors: Stephen B. Kaufman, Highland Park; Shelly Hyland, Crystal Lake; Michael A. Lesczynski, Gurnee; Calvin L. Bryant, Bartlett, all of Ill.

[73] Assignee: Health Tech Services Corporation, Northbrook, Ill.

[*] Notice: The portion of the term of this patent subsequent to Jun. 12, 2007 has been disclaimed.

[21] Appl. No.: 452,788

[22] Filed: Dec. 19, 1989

Related U.S. Application Data

[63] Continuation of Ser. No. 201,779, Jun. 2, 1988, Pat. No. 4,933,873, which is a continuation-in-part of Ser. No. 194,018, May 12, 1988, abandoned.

[51] Int. Cl.⁵ .......................... G10L 7/08; A61B 5/00
[52] U.S. Cl. .................................. 222/638; 128/630; 364/413.02
[58] Field of Search .................. 381/41–46; 364/513.5, 413.02–413.04; 367/198; 321/2–3, 15; 128/630; 368/10, 12

[56] References Cited

U.S. PATENT DOCUMENTS

| | | | |
|---|---|---|---|
| 3,369,697 | 2/1968 | Glucksman et al. | 221/9 |
| 3,395,829 | 8/1968 | Cogdell et al. | 221/15 |
| 3,552,381 | 1/1971 | Burns et al. | 128/2.05 |
| 3,651,984 | 3/1972 | Redenbach | 221/3 |
| 3,675,640 | 7/1972 | Gatts | 128/2.05 R |
| 3,722,739 | 3/1973 | Blumberg | 221/3 |
| 3,762,398 | 10/1973 | Schefke et al. | 128/2 R |
| 3,762,601 | 10/1973 | McLaughlin | 221/154 |
| 3,815,780 | 6/1974 | Bauer | 221/15 |
| 3,857,383 | 12/1974 | Sommerfield et al. | 128/20 |
| 3,911,856 | 10/1975 | Ewing | 116/121 |
| 3,917,045 | 11/1975 | Williams et al. | 194/4 C |
| 3,964,638 | 6/1976 | Diamauro | 221/3 |
| 3,968,900 | 7/1976 | Stambuk | 221/3 |
| 3,998,356 | 12/1976 | Christensen | 221/2 |
| 4,033,336 | 7/1977 | Murawski et al. | 128/2.05 R |
| 4,034,740 | 7/1977 | Atherton et al. | 128/1 B |
| 4,034,757 | 7/1977 | Glover | 128/260 |
| 4,053,951 | 10/1977 | Hudspeth et al. | 364/415 |
| 4,130,881 | 12/1978 | Haessler et al. | 364/900 |
| 4,207,992 | 6/1980 | Brown | 221/15 |
| 4,216,462 | 8/1980 | McGrath et al. | 364/413.03 |
| 4,223,801 | 9/1980 | Carlson | 221/3 |
| 4,227,526 | 10/1980 | Goss | 128/214 E |
| 4,258,354 | 3/1981 | Carmon et al. | 340/309.4 |
| 4,275,384 | 6/1981 | Hicks et al. | 340/309.4 |
| 4,360,125 | 11/1982 | Martindale et al. | 221/2 |
| 4,361,408 | 11/1982 | Wirtschafter | 368/10 |
| 4,367,955 | 1/1983 | Ballew | 368/10 |

(List continued on next page.)

FOREIGN PATENT DOCUMENTS 0251520 1/1988 European Pat. Off. .

OTHER PUBLICATIONS

Comarcher et al "A Micro-Computer Based System for the Management of the Critically Ill" (1978).

Comarchero et al. Solo: "An Interactive Microcomputer Based Bedside Monitor" (1979).

(List continued on next page.)

Primary Examiner—Emanuel S. Kemeny
Attorney, Agent, or Firm—Fuller, Ryan & Hohenfeldt

[57] ABSTRACT

An interactive patient assistance device houses first and second compartments for storing a first item and a second item away from access by the patient. First and second delivery mechanisms are associated with the first and second compartments for making the first stored item available to the patient in response to a first command signal and for making the second stored item available to the patient in response to a second command signal. The first and second items are delivered to the patient according to schedules stored in resident memory. The schedules may be altered by a prescribed command issued by the patient.

6 Claims, 15 Drawing Sheets

U.S. PATENT DOCUMENTS

| | | | |
|---|---|---|---|
| 4,370,983 | 0/1983 | Lichtenstein | 128/630 |
| 4,382,688 | 5/1983 | Machamer | 368/10 |
| 4,419,016 | 12/1983 | Zoltan | 368/10 |
| 4,448,541 | 5/1984 | Wirtschafter | 368/10 |
| 4,473,884 | 9/1984 | Behl | 364/479 |
| 4,483,626 | 11/1984 | Noble | 368/10 |
| 4,490,711 | 12/1984 | Johnston | 340/309.4 |
| 4,504,153 | 3/1985 | Schollmeyer | 368/10 |
| 4,526,474 | 7/1985 | Simon | 368/10 |
| 4,572,403 | 2/1986 | Benaroya | 221/3 |
| 4,573,606 | 3/1986 | Lewis et al. | 221/2 |
| 4,616,316 | 10/1986 | Hanpeter et al. | 364/413 |
| 4,653,474 | 3/1987 | Reithler | 128/1 R |
| 4,674,651 | 6/1987 | Scidmore et al. | 221/3 |
| 4,674,652 | 6/1987 | Aten et al. | 221/3 |
| 4,695,954 | 9/1987 | Rose et al. | 364/913 |
| 4,712,562 | 12/1987 | Ohayon et al. | 128/672 |
| 4,725,997 | 2/1988 | Urquhart et al. | 368/10 |
| 4,731,726 | 3/1988 | Allen | 364/416 |
| 4,748,600 | 5/1988 | Urquhart | 221/2 |
| 4,776,016 | 10/1988 | Hansen | 381/42 |
| 4,803,625 | 2/1989 | Fu et al. | 364/413.03 |
| 4,831,562 | 5/1989 | McIntosh | 364/569 |
| 4,933,873 | 6/1990 | Kaufman et al. | 364/513.5 |

OTHER PUBLICATIONS

Blum et al. "Protocol Directed Patient Care Using A Computer" (1980).

Rodbard et al. "A Data Management Program to Assist with Home Monitoring of Blood Glucose and Self Adjusting of Insulin Dosage for Patient with Diabetes Mellitus and their Physicians" (1984).

Kouchoukos et al. "Automated Patient Care Following Cardiac Surgery" (1971).

Hudson et al. "Microcomputer-Based Expert System for Clinical Decision-Making" (1981).

Worthman et al. "Quality Assessment in Emergency Medical Services Systems: The Criteria Mapping Method" (1979).

Greenfield et al. "The Clinical Investigation and Management of Chest Pain in an Emergency Department" (1979).

Sanders et al. "Micro-Computer Controlled Care System for the Severely Physically Impaired" (1984).

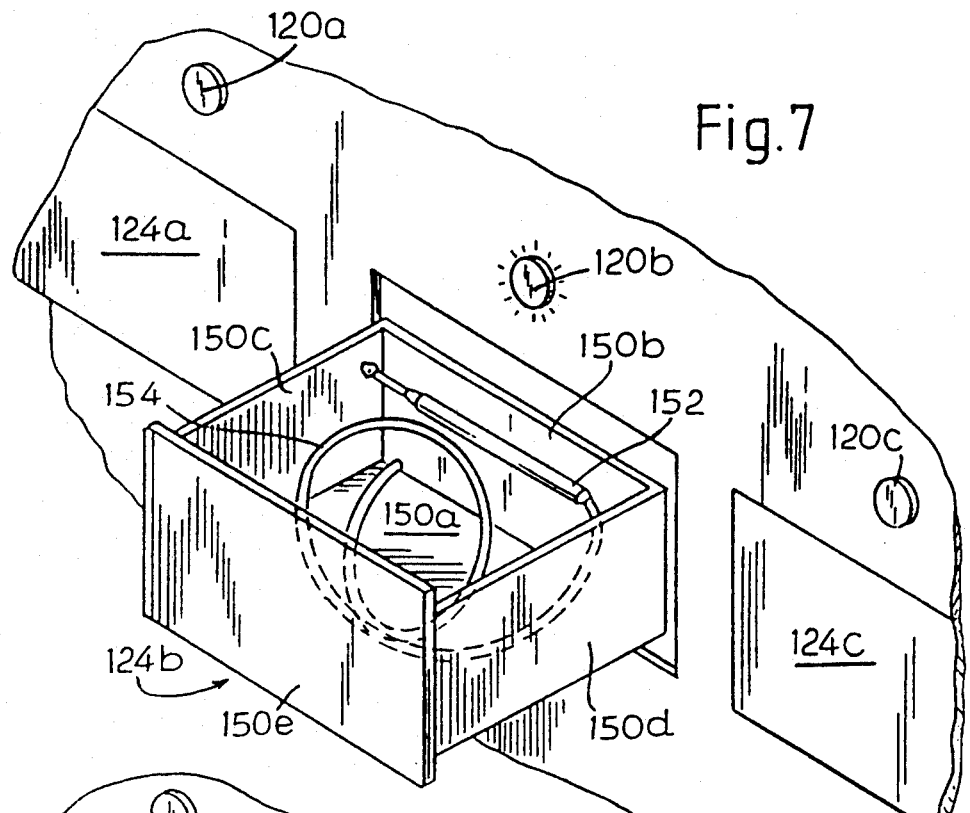
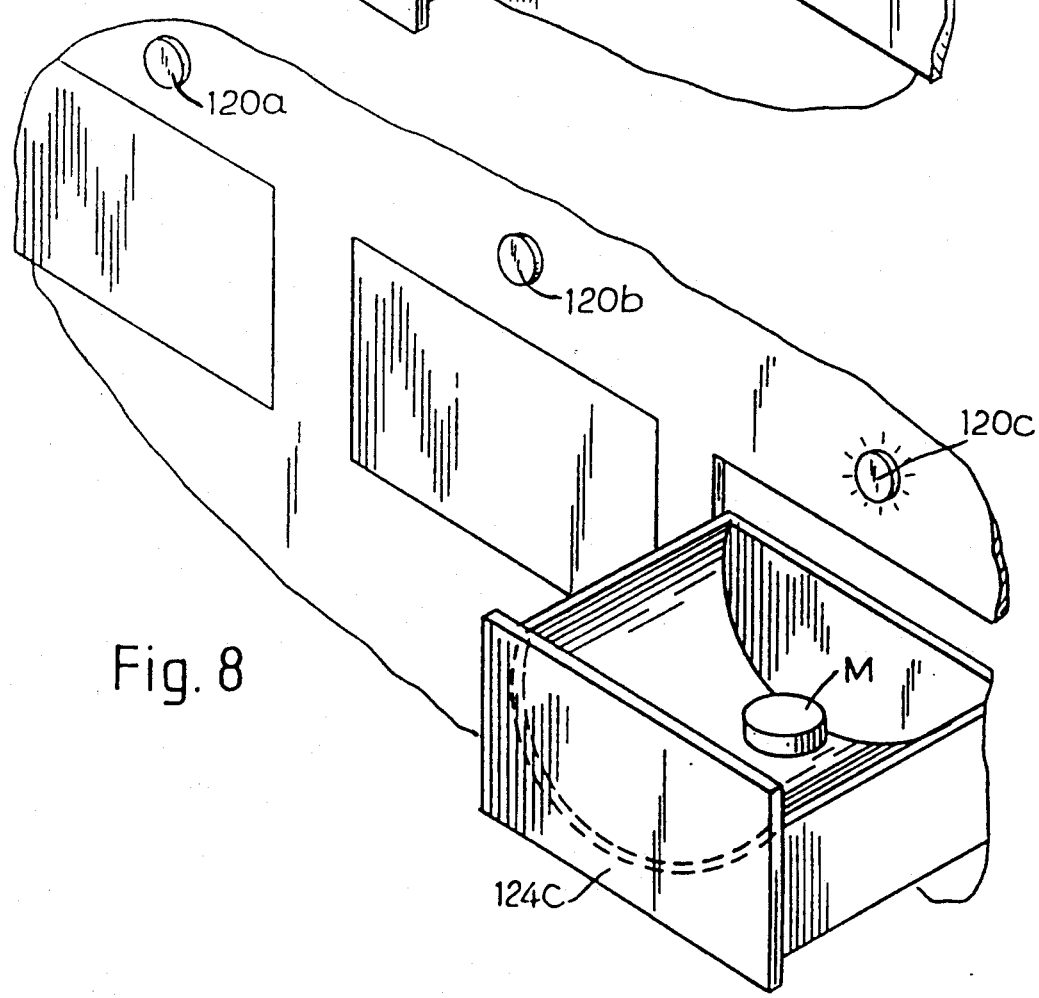

AN INTERACTIVE PATIENT ASSISTANCE DEVICE FOR STORING AND DISPENSING PRESCRIBED MEDICATION AND PHYSICAL DEVICE

REFERENCE TO RELATED PATENT APPLICATION

The present patent application is a continuation of U.S. application Ser. No. 07/201,779 filed Jun. 2, 1988 and entitled "An Interactive Patient Assistance Device", now U.S. Pat. No. 4,933,873 whic h was a continuation-in-part of patent application Ser. No. 194,018 filed May 12, 1988 now abandoned, entitled INDIVIDUAL ASSISTANCE SYSTEM and assigned to the same assignee as the present application.

FIELD OF THE INVENTION

The invention pertains to apparatus and devices for assisting individuals. More particularly, the invention pertains to a computer based system for providing at home or institutional assistance to a convalescing or injured patient.

BACKGROUND OF THE INVENTION

Over the last several years, there has been a substantial shortening of the period of time patients remain in hospitals. Reductions in hospital stays are directly related to the Federal Medicare Regulations governing reimbursements to hospitals and other institutions. These regulations impose strict limits on the number of hospital days, or institution days, for which Medicare will reimburse the hospital or institution.

Due to the shortened hospital stays, many patients are returning home in a debilitated or partially recovered condition. These patients often need assistance or reminders that medication should be taken, or that various measurements such as temperature or blood pressure should be made.

This situation is exacerbated by the fact that the size of the population which is over 65 years of age is continually increasing and will be increasing for the foreseeable furture. In addition, because of the improved health care delivery system in general, patients with chronic diseases are surviving for longer periods of time and leading relatively normal lives with intermittent outpatient intervention.

It has also been recognized that patients who need follow-up or who are convalescing at home can benefit from regular home monitoring. Such monitoring provides follow up information concerning the condition of the patient.

For instance, home monitoring can provide information concerning the long-term effectiveness of drugs. This information can in turn lead to altering, increasing or decreasing prescription requirements to more cost effectively obtain the desired result with the patient.

Home monitoring can also provide long-term trend information concerning patient vital signs. In extreme cases, home monitoring can result in immediate intervention to avoid a life threatening situation.

Thus, there continues to be a need for devices and apparatus which would be of assistance to homebound patients in a variety of ways. Further, there continues to be a need for such devices which can be provided cost-effectively.

SUMMARY OF THE INVENTION

In accordance with the invention, a patient assistance system is provided for repetitively interacting with an individual in need of assistance. The system can provide a variety of functions useful to an individual who may be debilitated or convalescing from an injury or an illness.

One aspect of the invention provides an interactive patient assistance device that includes a housing in which first and second compartments are located. These compartments serve to store a first item and a second item away from access by the patient. First and second delivery means are associated with the first and second storage means, respectively. The delivery means make the stored items available to the patient in response to prescribed command signals. Patient command means is also provided for receiving a interpreting a prescribed command made by the patient.

The device also includes first memory means for storing a first prescribed schedule for delivering the first stored item, as well as second memory means for storing a second prescribed schedule for delivering the second stored item. First control means issues the prescribed command signal to actuate the first delivery means for the first item in response to the prescribed schedule stored in the first memory means. Second control means issues the prescribed command signal to actuate the second delivery means for the second item in response to the prescribed schedule stored in the second memory means. Third control means is connected with the patient command means for altering a selected one of the prescribed schedules stored in the first and second memory means in response to a prescribed command made by the patient.

In a preferred embodiment, the patient command means includes speech recognition means for receiving and interpreting prescribed verbal commands made by the patient.

Also in a preferred embodiment, the first compartment stores a dosage of medication and the second compartment stores testing means usable for the patient for measuring a preselected health parameter.

In one embodiment, at least one of the delivery mechanism includes a drawer movable between a closed position within the housing and an opened position outside the housing. In this arrangement, the associated control means moves the drawer from its closed to its opened position.

BRIEF DESCRIPTION OF THE DRAWINGS

FIG. 7 is an enlarged fragmentary view in perspective of a portion of the thermometer storage/delivery unit;

FIG. 8 is an enlarged fragmentary view in perspective of a portion of the product storage/delivery unit;

DETAILED DESCRIPTION OF THE PREFERRED EMBODIMENTS

Figure 1:
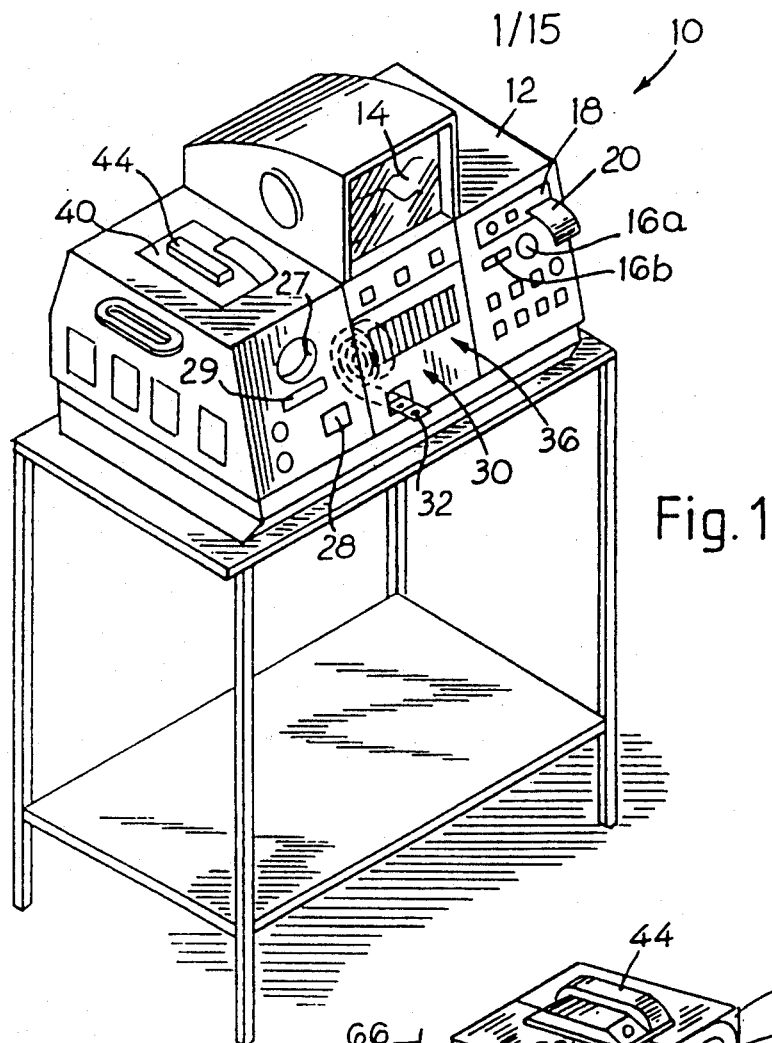
FIG. 1 is a perspective view of a stationary recordkeeping and medication delivery interactive system in accordance with the present invention.

While this invention is susceptible of embodiment in many different forms, there are shown in the drawing and will be described herein in detail specific embodiments thereof with the understanding that the present disclosure is to be considered as an exemplification of the principles of the invention and is not intended to limit the invention to the specific embodiments illustrated.

FIG. 1 is a perspective view of a patient assisting system 10 in accordance with the present invention. The system 10 includes a housing 12. Carried by the housing 12 is a video display unit 14.

The system 10 includes a clock/calendar unit 16. The clock/calendar unit 16 can be a digital unit with an integrally formed display.

The housing 12 carries an audible alarm 16a. The audible alarm 16a can be actuated by the electronic clock/calendar unit 16. The clock/calendar unit can be a programmable unit in which a schedule can be established to identify a variety of scheduled activities during a 24-hour interval. A display 16b is also coupled to the clock/calendar unit 16.

The housing 12 also carries a hard copy printer 18 capable of generating hard copy 20. The copy 20 can include information pertaining to medication schedules, delivered medication, test results or instructions as may be desired.

The system 10 can also include a blood pressure monitoring cuff storeable in a region 24 of the system 10. The same cuff can be used for pulse rate detection as well.

The system 10 can also include a thermometer 28 coupled thereto The thermometer 28 can be drawn from the system 10 and used by the patient to provide an indication of corporal body temperature. The thermometer 28, the blood pressure cuff and the pulse rate sensor can be used to provide feedback to the system 10 concerning patient related characteristics. Temperature and blood pressure measurement values can be displayed using readouts 29.

The system 10 also includes a pharmaceutical dispenser 30. The pharmaceutical dispenser 30 can under control of the system 10 dispense medication on a strip 32 in accordance with a schedule maintained by the programmable clock/calendar unit 16.

The medication on the strip 32 can be dispensed in combination with either a printed reminder which can be printed by the printer 18 on the strip 20 or in combination with a verbal reminder. A voice synthesizer and recognition unit 36 carried by the housing 12 can provide audio reminders to the patient that a scheduled time for taking a medication has arrived. The unit 36 can provide audible feedback from the patient to the syste 10.

For example, the voice synthesizer and recognition unit 36 can detect statements made by the patient requesting assistance. These statements can include requests for help if the patient is in need of outside assistance. Alternately, the voice synthesizer and recognition unit 36 can detect requests by the patient to display information on the display 14 or to provide the appropriate medication. Finally, the voice synthesizer and recognition unit 36 can be used by the patient to establish the schedule to be maintained by the programmable clock/calendar unit 16.

It will be understood that in addition to detecting blood pressure, heart rate and body temperature, the system 10 could provide facilities for detecting blood gas levels as well as carrying out other types of non-invasive diagnostic tests. For example, one type of diagnostic testing that can be carried out in connection with the system 10 make use of known oximetry probes. Such probes can be attached to the ear lobe or finger of the patient and provide for continuous or intermittant reading of oxygen saturation levels in the blood.

The system 10 also incorporates a modem 40 which can be utilized in combination with an automatic dialer unit 42. The modem 40 could incorporate a standard type of telephone handset 44 if desired. By incorporating a handset 44, the system 10 can provide for a voice communication between the patient and a remote location.

By means of the modem 40, the system 10 can communicate with a remote medical center over the telephone system. Information which has been accummulated in the system 10 concerning patient activity or the results of diagnostic testing can be automatically transmitted via the modem 40 and the telephone system to a remote medical center computer for analysis. The results of such analysis can be used to determine whether or not further intervention, such as changing the medication schedule or the type of medication, is desirable.

The system 10 can also include a magnetic recording system. The recording system can record, on a relatively long-term basis, results of diagnostic tests, information concerning patient activity, dispensed medication and any other information of value in improving the quality of patient care.

The various elements of the system 10 function with a control unit 46. The control unit 46 could include a programmed computer.

Figure 2:
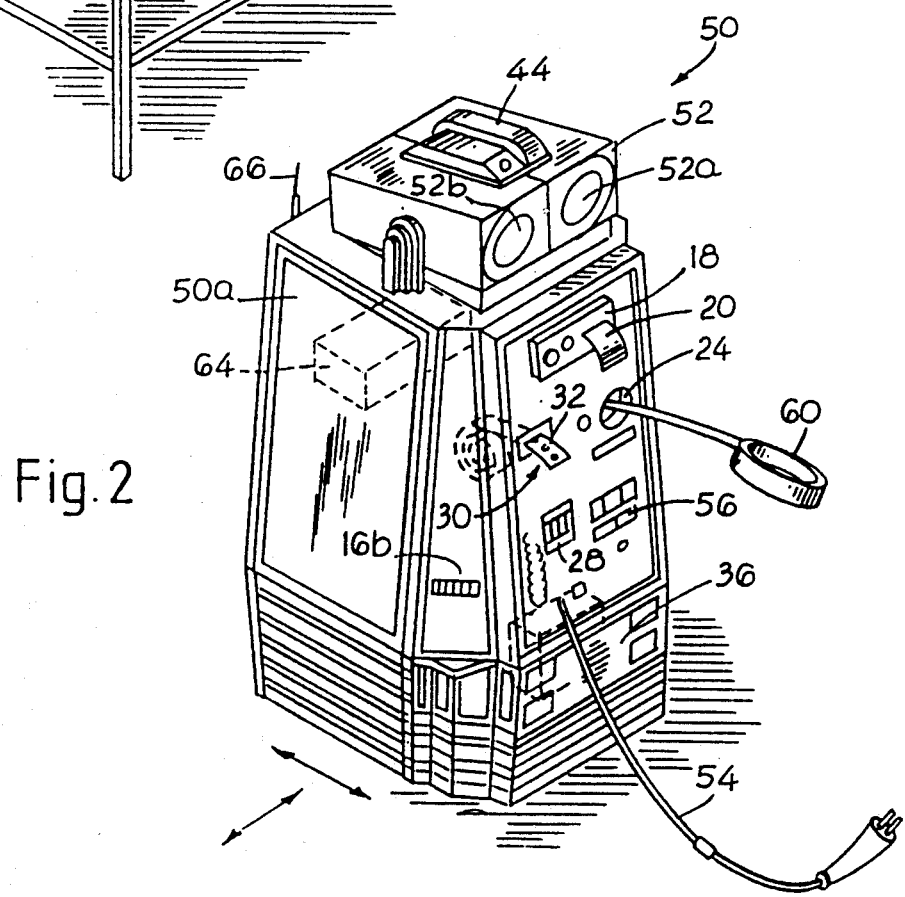
FIG. 2 is a perspective view of a moveable recordkeeping and medication delivery interactive system in accordance with the present invention.
Figure 3:
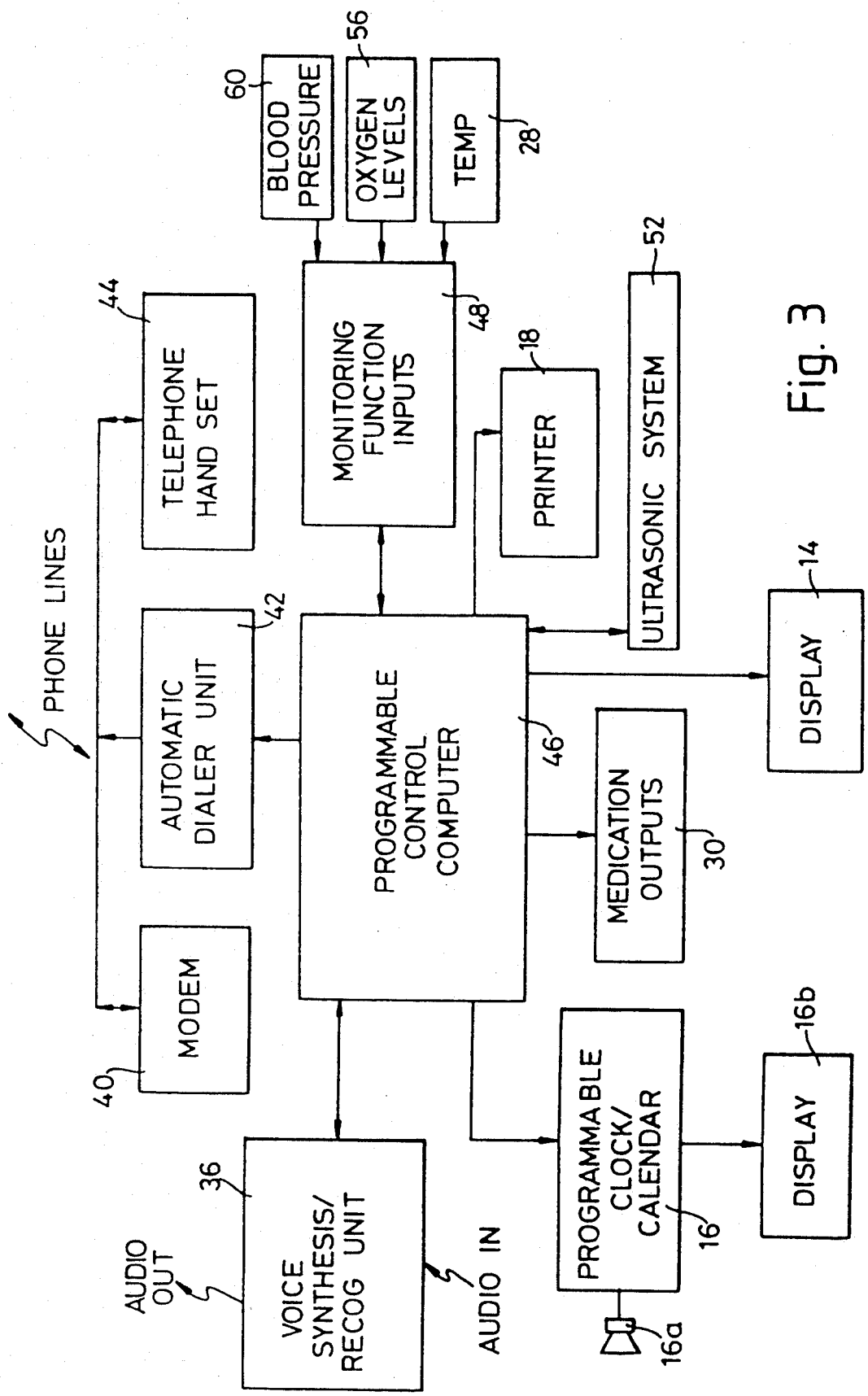
FIG. 3 is a block diagram schematic of an electronic system in accordance with the present invention.

FIG. 2 illustrates a perspective view of an alternate embodiment 50 of the system 10. The system 50 includes many of the functions and capabilities previously described with respect to the system 10. Such elements are identified using the same identification numerals as were used with respect to the system 10.

In addition, the system 50 provides additional capabilities and functions not present in the system 10. The system 50 in contradistinction to the system 10 is moveable under the command of the internal programmed control computer 46. The moveability of system 50 permits it to move toward the bedside or chair of the patient for ease of interaction with the patient.

Control over the movement of the system 50 by the computer 46 is effected by an ultrasonic system 52. The ultrasonic system 52 includes both a transmitter and a receiver 52a and 52b respectively. The ultrasonic system 52 can detect transmission from a patient-carried transmitter. The patient-carried transmitter can be used to inform the system 50 of the location of the patient. It can also be used to detect whether or not the patient is ambulatory and whether or not the patient has had an accident and has fallen and is in need of additional assistance.

The ultrasonic system 52 can also determine distance, range and proximity to objects for the purpose of collision avoidance. The ultrasonic system 52 also permits the patient assisting system 50 to safely move within a specified range near the patient.

The system 50 also includes a nasal cannula 54 usable in connection with administering oxygen therapy. Further, the system 50 can also include a probe 56 for measuring saturated oxygen levels in the blood, as previously discussed. Such probes, such as 56, are noninvasive and can readily be affixed by the patient to the appropriate corporal member.

The system 50 also includes a digital blood pressure sensing cuff 60 which can be removed from the storage region 24. The patient can apply the cuff 60 to an arm or finger or any other appendage. Under control of the system 50, the cuff 60 can be automatically inflated, the results of the blood pressure measurement can be detected by means of the monitoring function input interface 48. The cuff 60 can then be deflated and removed by the patient for storage in the region 24.

Simultaneously with detecting blood pressure by means of the cuff 60, the patient's pulse rate can also be detected.

The system 50 includes the voice synthesis and recognition unit 36 which provides an audio communication and control path between the patient and the system 50. A battery 64 is carried within the housing 50a for the purpose of powering the unit 50. The battery 64 can be a rechargeable type which can be recharged during periods of patient inactivity, such as night.

If desired, the handset 44 can be of the cordless type. In this instance, the system 50 would also carry a transmission/reception antenna 66.

It will be understood that the system 50 functions at all times under the control of the programmable unit 46 to insure proper carrying out of the above described functions. Further, by means of the voice synthesis and recognition unit 36 the patient is always able to provide verbal commands to the unit 50.

Figure 4:
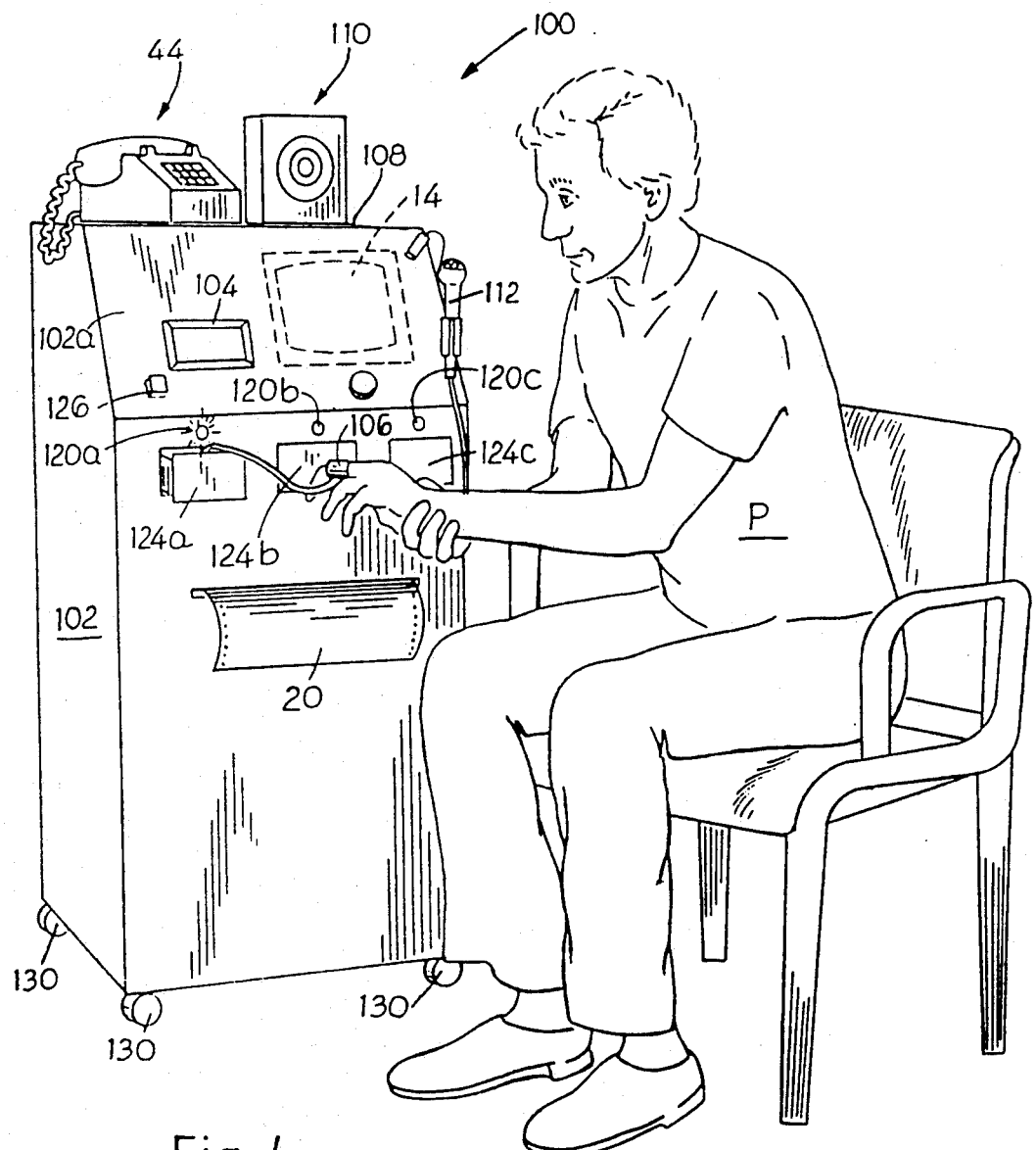
FIG. 4 is an overall perspective view of a system in accordance with the present invention interacting with a patient.

Further in accordance with the invention, FIG. 4 illustrates as an alternate embodiment, a system 100 in accordance with the principles of the present invention. The system 100 is being utilized by a patient P for purposes of carrying out a diagnostic test. Many of the elements of the system 100 correspond to elements of the system 10 and the system 50. Corresponding elements have been identified with the same identification numerals as were used in FIGS. 1 and 2.

The system 100 includes a housing 102. The housing 102, at an upper surface 102a, can support an optional display unit 14, indicated in phantom The housing 102 also carries an alphanumeric display 104. The alphanumeric display 104 can be used to conveniently display the results of various diagnostic tests which can be performed by the system 100.

In particular, the system 100 is illustrated in FIG. 4 with the patient P using a finger type blood pressure and pulse rate cuff 106. The cuff 106 can be used to detect the blood pressure and pulse rate of the patient P.

Supported on an upper surface 108 of the housing 102 is a telephone corresponding to the telephone 44. It will be understood that a variety of different telephones can be used without departing from the spirit and scope of the present invention.

Also carried on the surface 108 is a loudspeaker 110 which is coupled to the voice synthesis and recognition unit 36 discussed previously. A hands-free microphone 112 is also provided, coupled to the voice synthesis and recognition unit 36, for purposes of audio input by the patient P.

The housing 102 also supports a plurality of visual indicators 120a, 120b and 120c. The indicators 120a, 120b and 120c are usable in conjunction with a plurality of moveable storage/delivery units 124a, 124b and 124c.

The storage/delivery units 124a, 124b and 124c can be used for storage and delivery of a plurality of different items. For example, the unit 124a is illustrated in the system 100 as being the storage/delivery unit for the finger type cuff 106. The indicator 120a is utilized to prompt the patient P to the fact that the unit 124a has been released and the cuff 106 should be removed therefrom and inserted on the patient's finger for purposes of conducting a diagnostic test.

The unit 124b can be used for storage and delivery of a thermometer. The unit 124c can be used for storage and delivery of prescheduled products. The products can include medications in either liquid or solid form.

It will be understood that the types of apparatus and/or products, described above, utilized with the units 124a, 124b and 124c are merely exemplary. The exact type of apparatus stored or product delivered is not a limitation of the present invention.

The housing 102 also carries a manually operable, illuminatable signaling button or switch 126. The button or switch 126 can be used by the patient P to inform the system 100 that various activities have taken place or that various conditions have been met.

For example, the button or switch 126 can be used to prompt the system 100 to the fact that the patient has placed the cuff 106 on a finger and is ready for a blood pressure measurement to be made. Similarly, the switch 126 can be used to prompt the system 100 to the fact that the thermometer has been properly positioned and a temperature reading can be made. Finally, the button or switch 126 can be used to prompt the system 100 to the fact that a product, such as a medication, has been removed from the unit 126 and has been taken by the patient P.

While the system 100 has been illustrated in FIG. 4, supported on a plurality of rollable casters 130, it will be understood that, in accordance with the embodiment previously discussed in FIG. 2, the system 100 could be provided with a motorized unit for purposes of movement.

Figure 5:
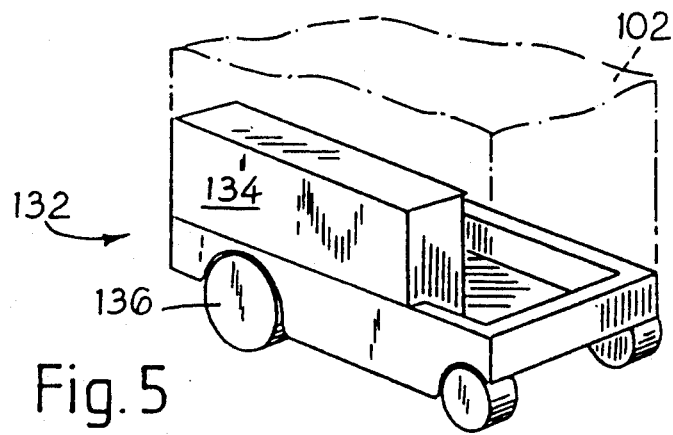
FIG. 5 is a fragmentary perspective view of the system of FIG. 4 supported on a powered module for movement.

FIG. 5 illustrates an exemplary motorized unit 132. The unit 132 carries the housing 102. The unit 132 includes a motor, control electronics and power source 134. The unit 134 can be mechanically coupled to drive wheels 136 for the purpose of moving the system 100 toward or away from the patient P.

Figure 6:
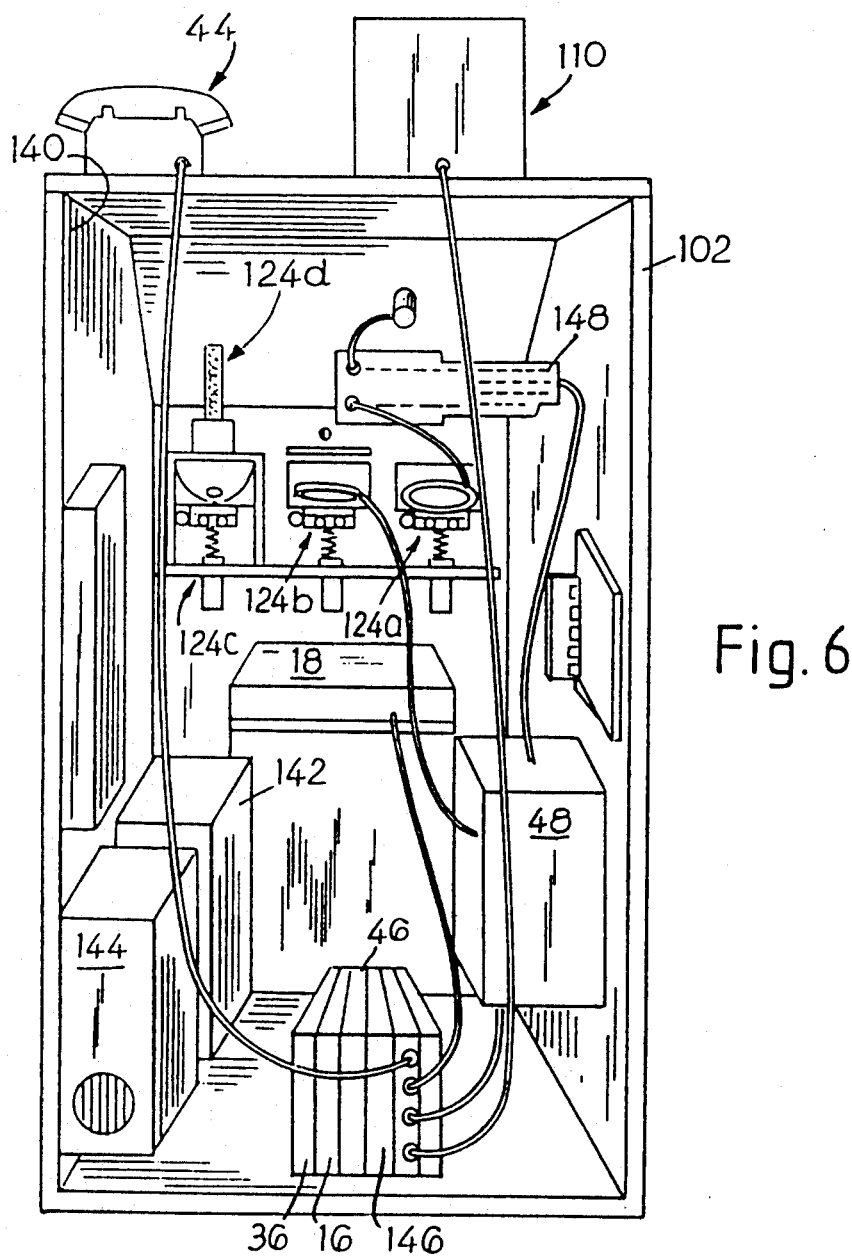
FIG. 6 is a rear elevational view of the system of FIG. 4.

FIG. 6 is a view of the rear of the housing 102 illustrating various components of the system 100. The housing 102 defines an interior region 14 wherein the components of the system 100 are carried.

The system 100, as discussed previously with respect to FIGS. 1 and 2 includes a programmable control computer 46. The computer 46 can be of a type comparable to IBM[R]-PC-XT or other computer system capable of performing multi-tasking. The unit 46 can include an interface for driving the display 14, if present, by the system 100. The unit 46 can also include the programmable clock/calendar unit 16.

The unit 46 can also include a disc drive controller.

Disc storage 142 can be located within the housing 102 adjacent the computer 46. The disc storage 142 can include a hard drive and one or more floppy drives depending on the desired capacity of data storage.

The computer 46 can also include the modem 40. The modem 40 could be for example a 1200 baud Hayes brand modem.

Adjacent the disc storage 142 is a system power supply 144. The supply 144 can include a rechargeable battery.

The voice synthesis/recognition unit 36 is also located adjacent the control computer 46. The voice synthesis/recognition unit 36 could be for example, a Texas Instruments Recognition and Speech Unit Model TI-2245186-001.

An interface card 146 is also provided adjacent the control computer 46. The interface card 146 provides part of the circuitry used for driving solenoids to control the units 124a, 124b or 124c as well as the displays 120a, 120b and 120c. For example, the unit 146 could be a Quatech Analogue input card or equivalent as would be known by those of skill in the art.

The housing 102 also carries electrical interface circuitry 148. The circuitry 148 converts signals from the measurement cuff 106 to electrical signals usable by the monitoring function unit 48.

The housing 102 also carries the printer 18 for a generation of hard copy records 20 or graphical diagrams.

FIG. 7 is a perspective, fragmentary, view illustrating the storage/delivery unit 124b in the delivery position. In the exemplary unit illustrated in FIG. 7, the unit 124b is a multi-sided drawer with a bottom 150a joined by four sides 150b, 150c, 150d and 150e.

It will be understood that the exact shape of the storage/delivery unit 124b is not a limitation of the present invention. A variety of different shapes could be used which would function in substantially the same way to produce substantially the same results.

Carried within the unit 124b is a thermometer 152. The thermometer 152 is coupled by conductors 154 to the monitoring function interface unit 48.

As illustrated in FIG. 7, the indicator 120b has been energized indicating to the patient P that the system 100 is awaiting the withdrawal of the thermometer 152 from the unit 124b and the subsequent actuation by the patient of the control button 126.

As illustrated in FIG. 4, the unit 124b has a first, or closed, position. The unit 124b also has a second, or open, position as illustrated in FIG. 7. Each of the units 124a and 124c has corresponding first and second positions.

FIG. 8 illustrates the unit 124c in its second, or open, position. The indicator 120c has been energized indicating to the patient P that a product such as medication M in unit 124c is available and can be accessed in the drawer 124c. It will be understood that while medication M has been illustrated in solid, or pill form, in FIG. 8 that the exact form of the dispensed product is not a limitation of the present. The product need not be a medication or alternately could be in liquid form.

Figure 9:
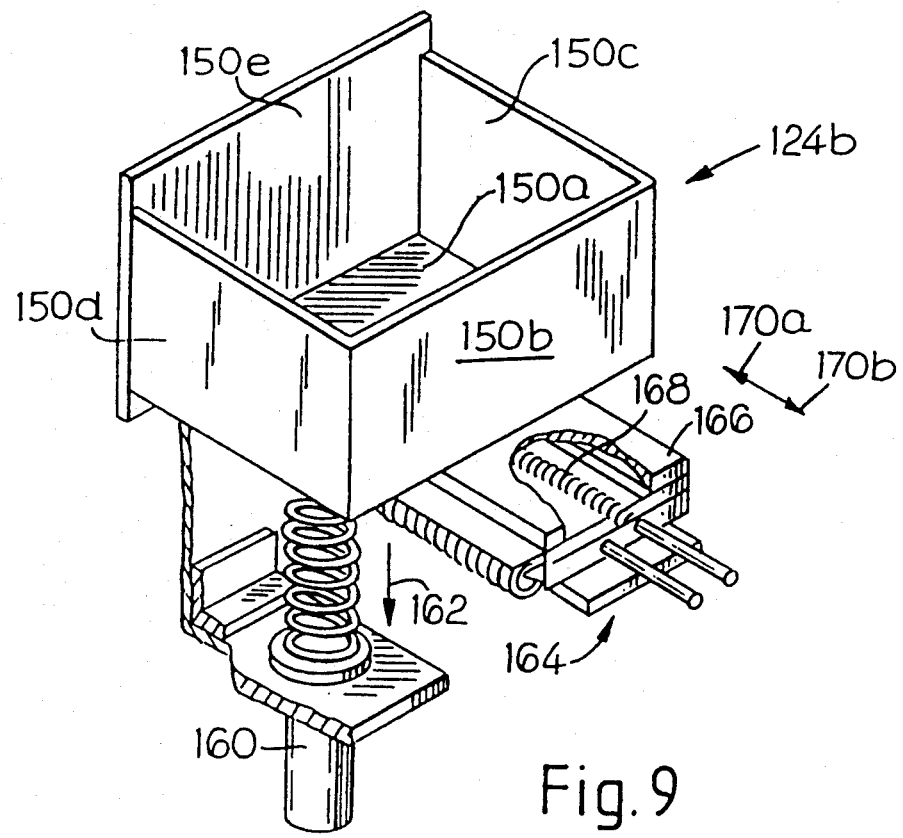
FIG. 9 is an enlarged fragmentary view in perspective, partly broken away, of the actuating mechanism of the storage/delivery unit of FIG. 7.

FIG. 9 is a fragmentary enlarged view of the unit 124b along with an associated electrically operated release mechanism 160. The release mechanism 160 could be an electrically actuated spring biased solenoid of a conventional type.

When energized, a locking member, or armature, of the solenoid 160 retracts by moving in an unlocking direction 162. Once the solenoid 160 has retracted, the unit 124b is forced to its second, or open, position by means of a spring biasing unit 164.

The unit 164 includes a support housing 166. The housing 166 includes an internal, compressed, biasing spring 168. The spring 168, in response to the solenoid 160 having energized its armature which moves in the releasing direction 162, forces the unit 124b to move in a direction 170a from the first, closed position to the second, open position. The unit 124b can be returned to the first, or closed position by manually forcing it in a direction 170b until the solenoid 160 relatches it.

Figures 10A, 10B:
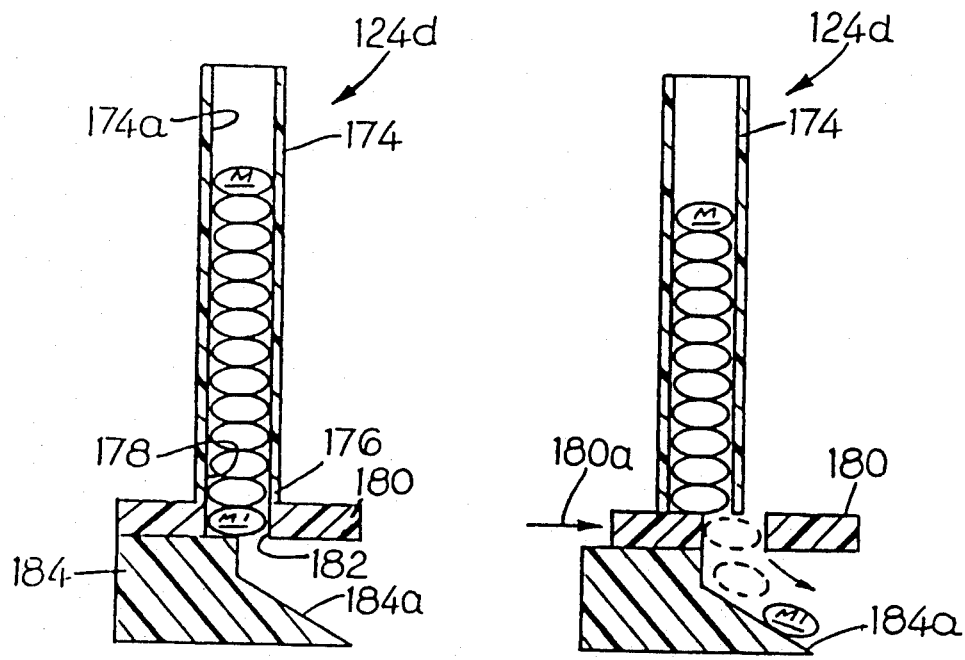
FIG. 10a is a view in section illustrating a first or inactive state of the product dispensing mechanism.
FIG. 10b is a view in section of the product dispensing mechanism in a second or dispensing state.
Figure 11A:
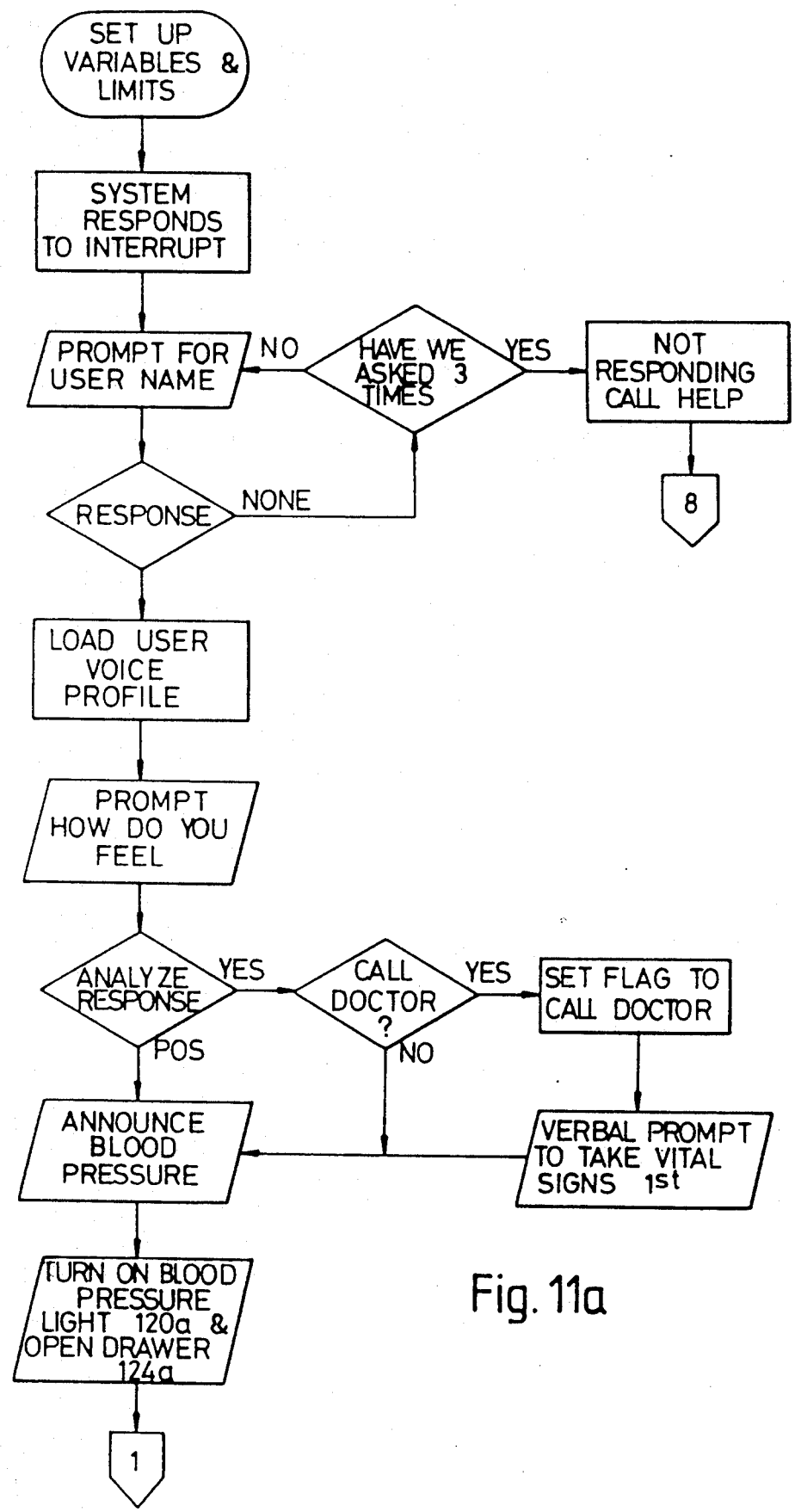
FIGS. 11a–11e, taken together, are a flow diagram of the software and interactions of the system of FIG. 4.
Figure 11B:
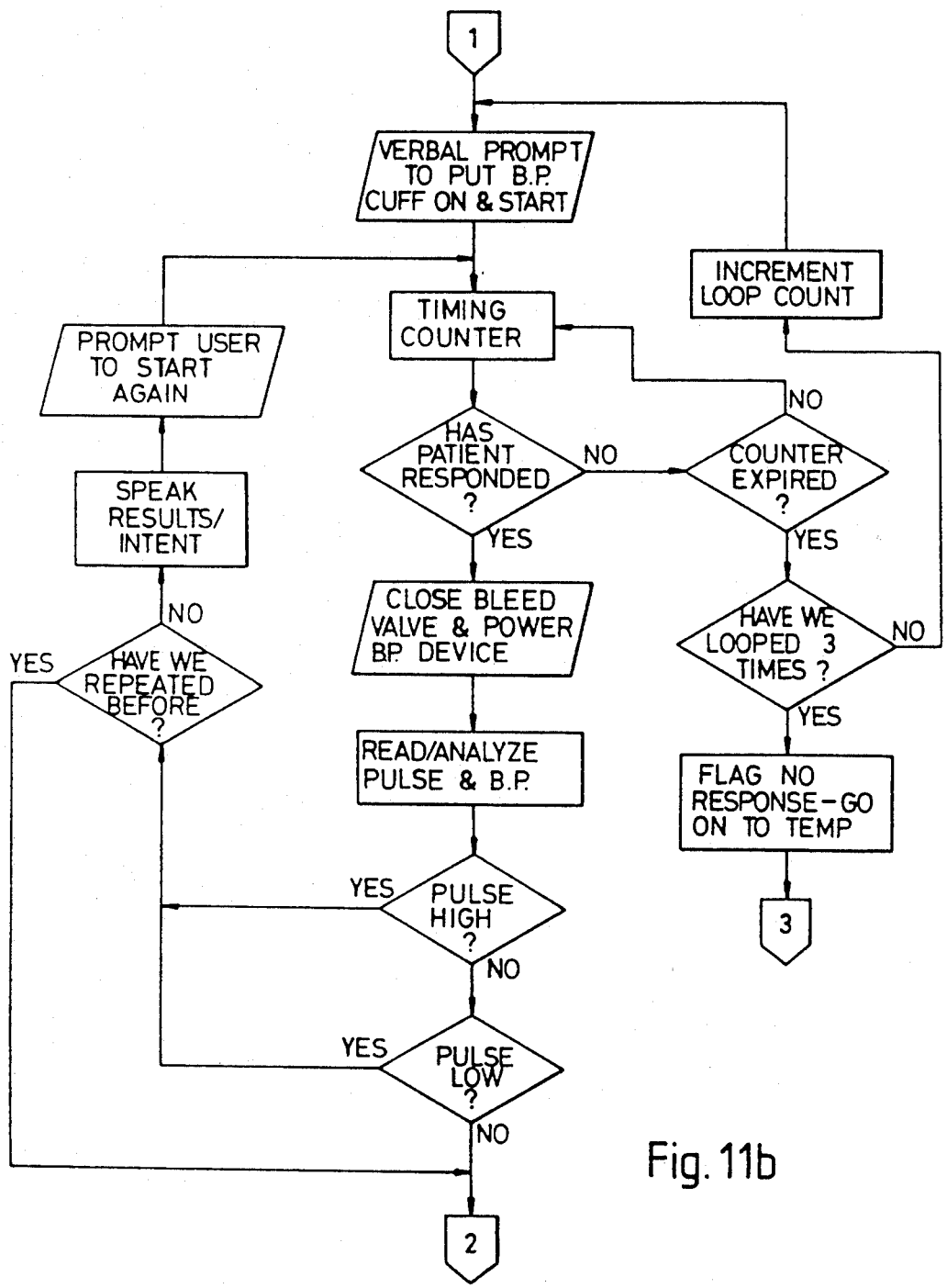
Figure 11C:
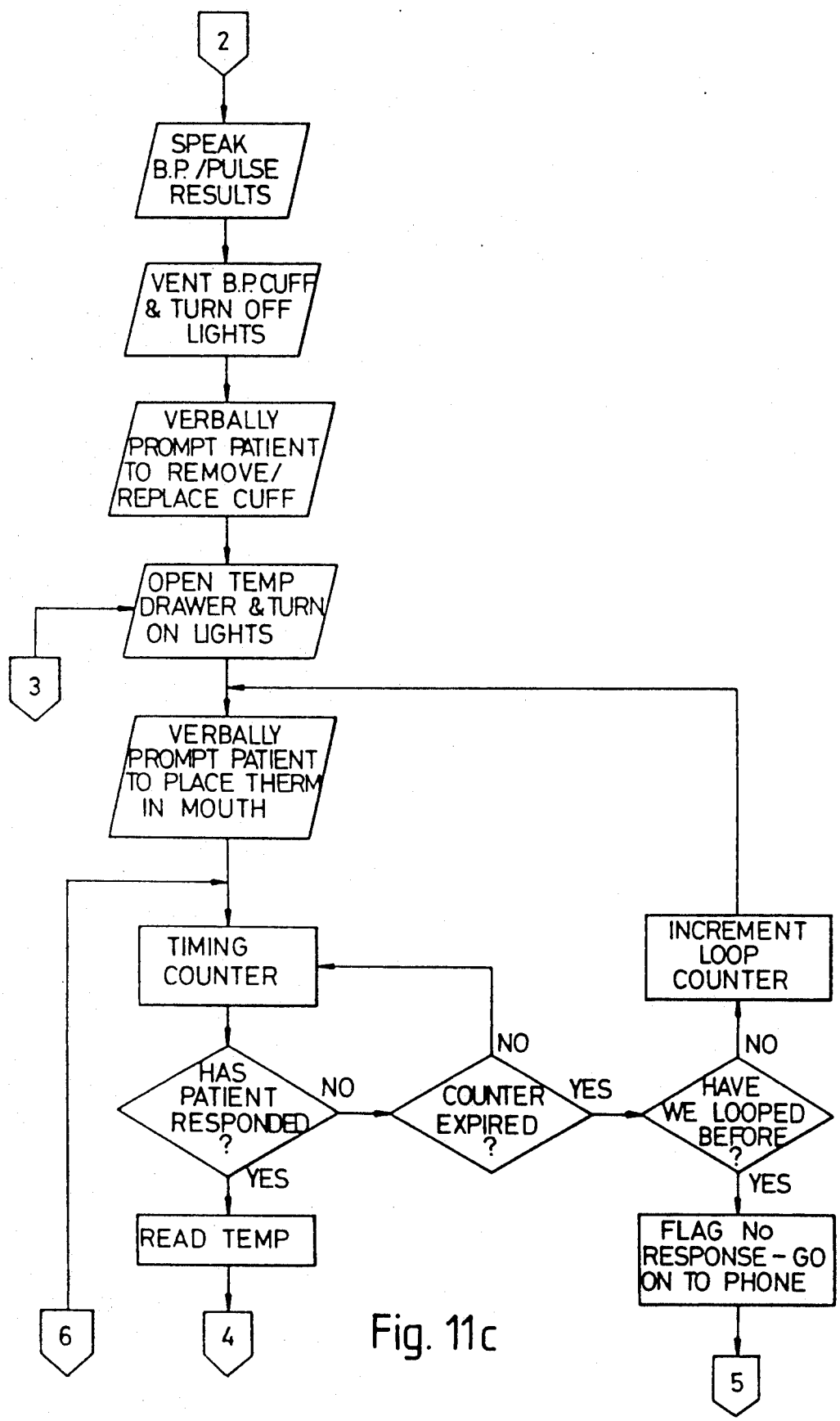
Figure 11D:
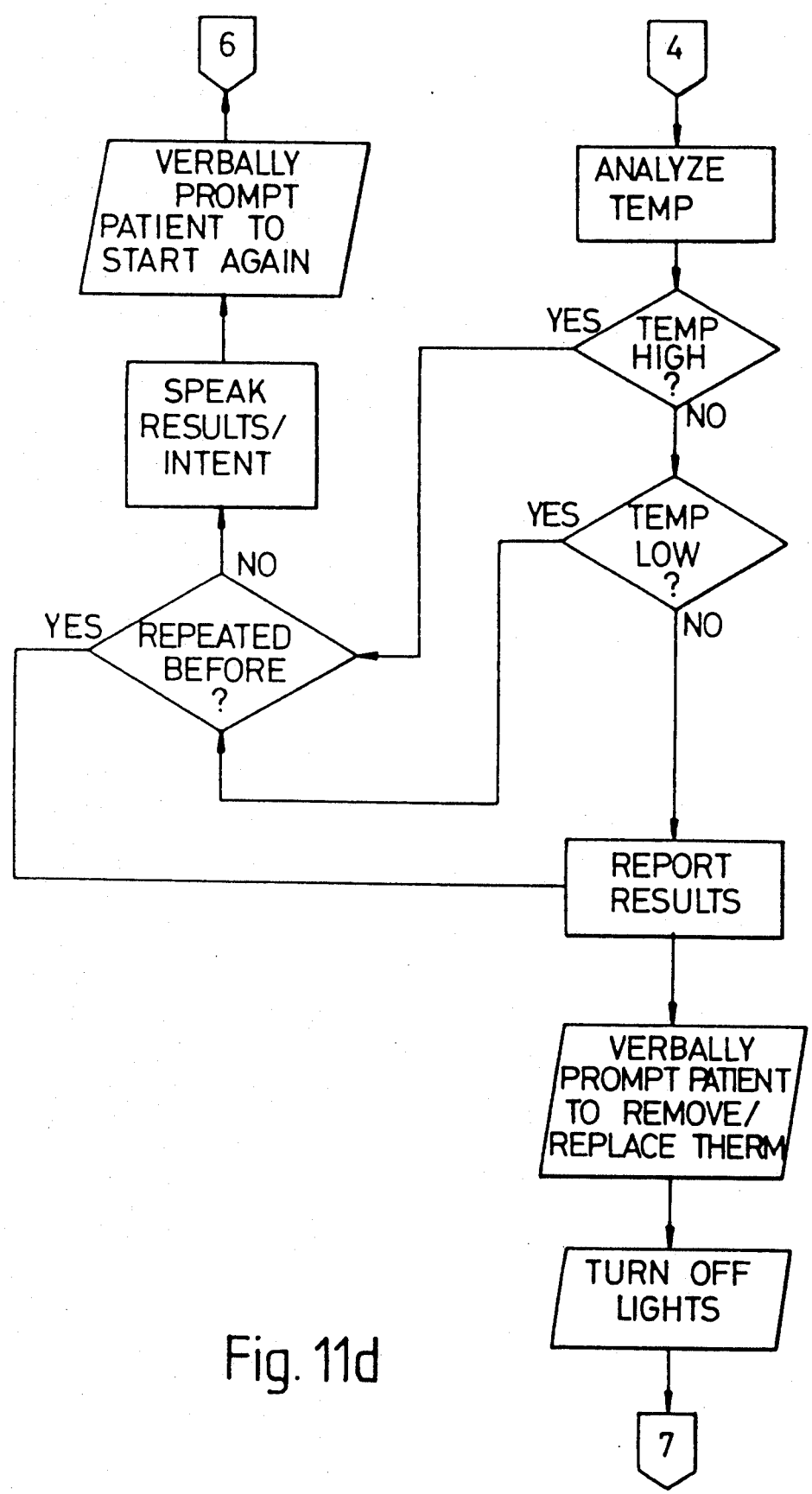
Figure 11E:
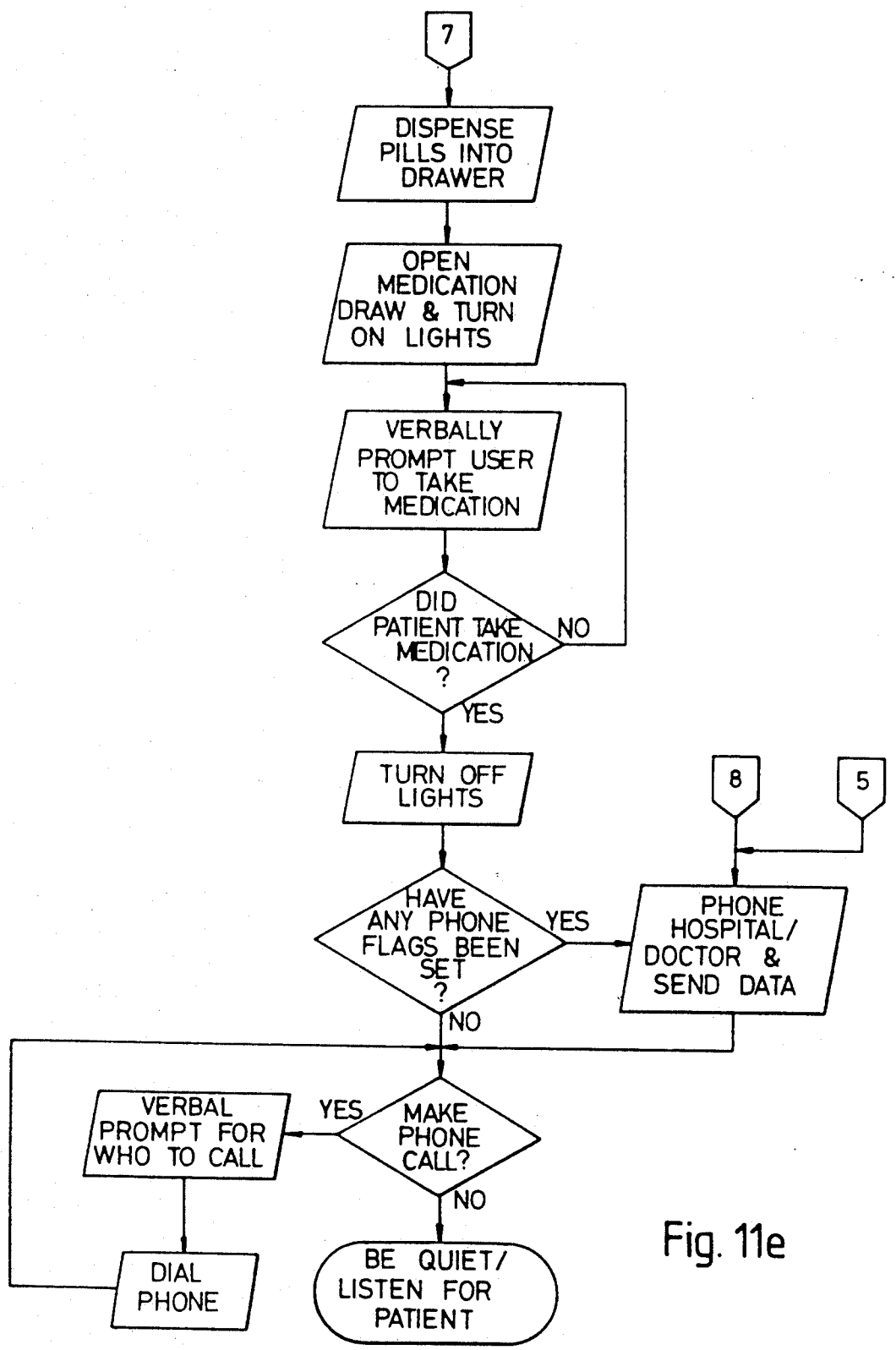

FIGS. 10A and 10B are enlarged fragmentary sectional views illustrating the structure and operation of the product dispensing unit 124d. The unit 124d includes a housing 174 which defines a product containing volume 174a.

Within the product containing volume 174a can be stored a plurality of products corresponding to the medication M. In the illustrative embodiment of FIGS. 10A and 10B, the product corresponds to individually dispensed medication units or pills.

The housing 174 has a lower open end 176. The end 176 defines a product releasing opening 178 therein. A single product releasing index member 180 is positioned adjacent the end 176 of the housing 174.

The index member 180 also defines a single product containing region 182 therein. Affixed to the housing 174 is a fixed delivery member 184. The delivery member 184 includes a product delivery ramp 184a.

As illustrated in FIG. 10B, the index plate 180 can be moved laterally in a direction 180a in response to the control unit 46 actuating an electrical solenoid. The movement of the indexing unit 180 dispenses the product M1 located in the region 182 as illustrated in FIG. 10B. At the same time, movement of the indexing plate 180 blocks other products M in the region 174a from being dispensed simultaneously. The product M1 when released from the indexing member 180 can slide down the delivery shut 180a and into the unit 124c for subsequent removal and use by the patient P.

At the end of the release cycle the indexing unit 180 returns to its rest position illustrated in FIG. 10A by moving opposite to the direction 180a. The cycle may then be repeated. The next time the solenoid is energized, the index unit 180 will again move in the direction 180a and dispense a single product to the unit 124c.

It will be understood that the exact structure of the dispensing mechanism 124b is not a limitation of the present invention. Nor, is the type of product to be dispensed a limitation of the present invention.

FIGS. 11A through 11E, taken together, are a flow diagram illustrating the steps of a method of operation of the system 100 and its interactions with the patient P. The flow diagram of FIGS. 11A-11E also defines the control program to be used with the control computer 46 to implement the functioning of the system 100.

Attached hereto as an Addendum is a listing of a program usable with the system 100. The first group of instructions, up to line 400 of the Addendum, is a plurality of interface sub-routines to enable the processor 46 to interact with various of the interface devices. The portion of the program from line 400 on to the end is written in BASIC and is the control program for the system 100.

Figure 12:
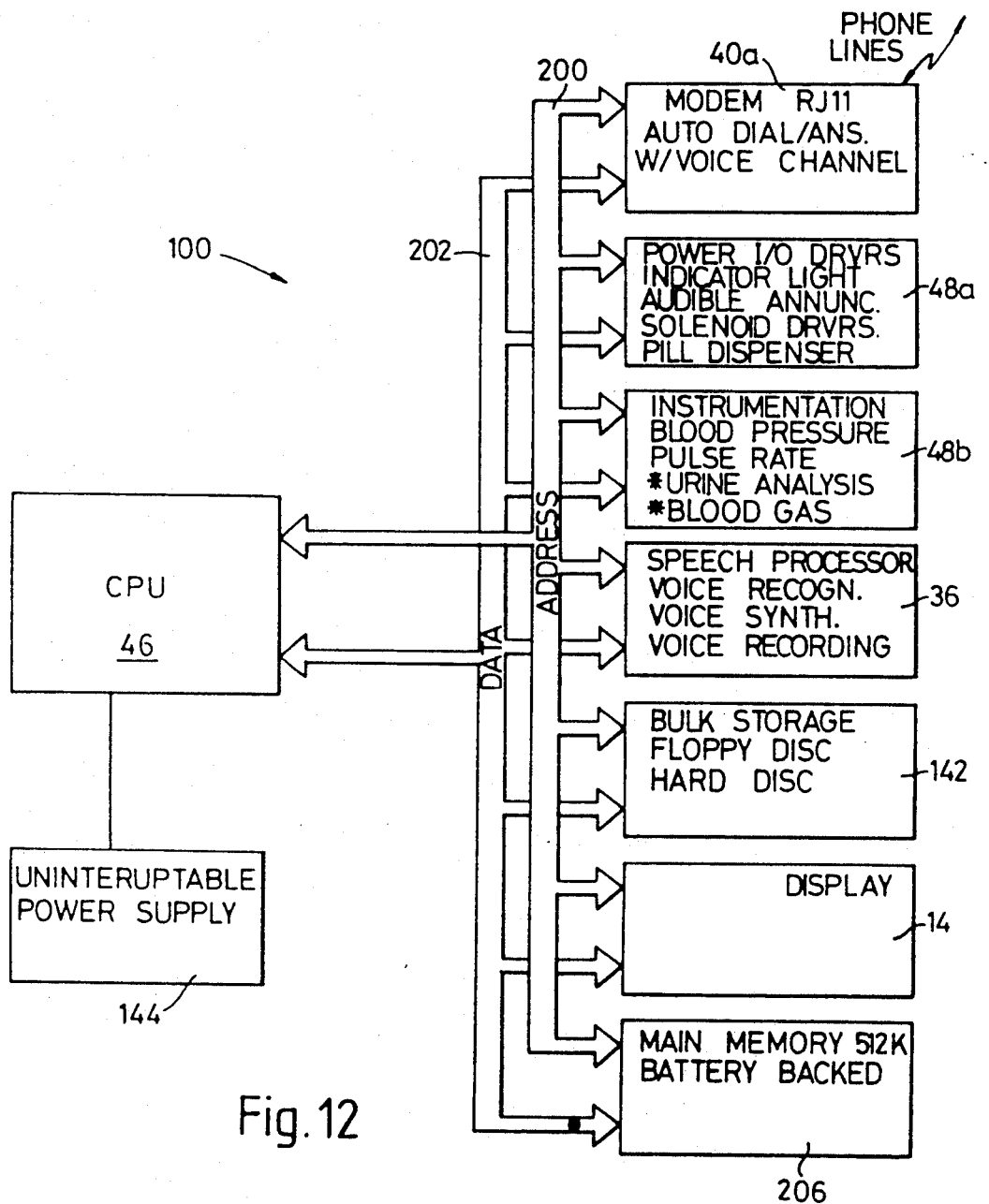
FIG. 12 is an overall block diagram schematic of the electronic control system of the system of FIG. 4.

FIG. 12 is a block diagram schematic of the system 100. As noted previously, the processor 46 or central processing unit is comparable to an, IBM$^R$-PC-XT class computer. The power supply 144 coupled thereto is of an uninterruptable type having a self-contained rechargeable battery.

The processor 46 is coupled via an address bus 200 and a data bus 202 to a plurality of input/output units. Among those units is a modem 40a which includes automatic dial and answer as well as a voice channel for audio communication.

The address bus 200 and data bus 202 are also coupled to solenoid drive circuitry, indicator drive circuitry and medication solenoid drive circuitry 48a. The address bus 200 and the data bus 202 are also coupled to instrumentation interface circuitry 48b. The instrumentation interface circuitry can include the blood pressure/pulse rate cuff 106 thermometer 152, along with optional blood gas analyzer 56 and urine analyzer.

The speech processor circuitry including the voice synthesis/recognition unit 36 as well as voice recorded circuitry is also coupled to both the address bus 200 and the data bus 202. The system 100 also utilizes a 10 megabyte hard disc and a 360 K-byte floppy disc represented by element 142. If desired, the optional display 14 will also be coupled to the address bus 200 and the data bus 202.

The display 14 could also include a keyboard for operator input. Instead of a keyboard, the display 14 could incorporate a touch sensitive screen.

Finally, the system 100 includes 512 K-bytes of main random access memory 206 which utilizes the available battery backup.

Figure 13:
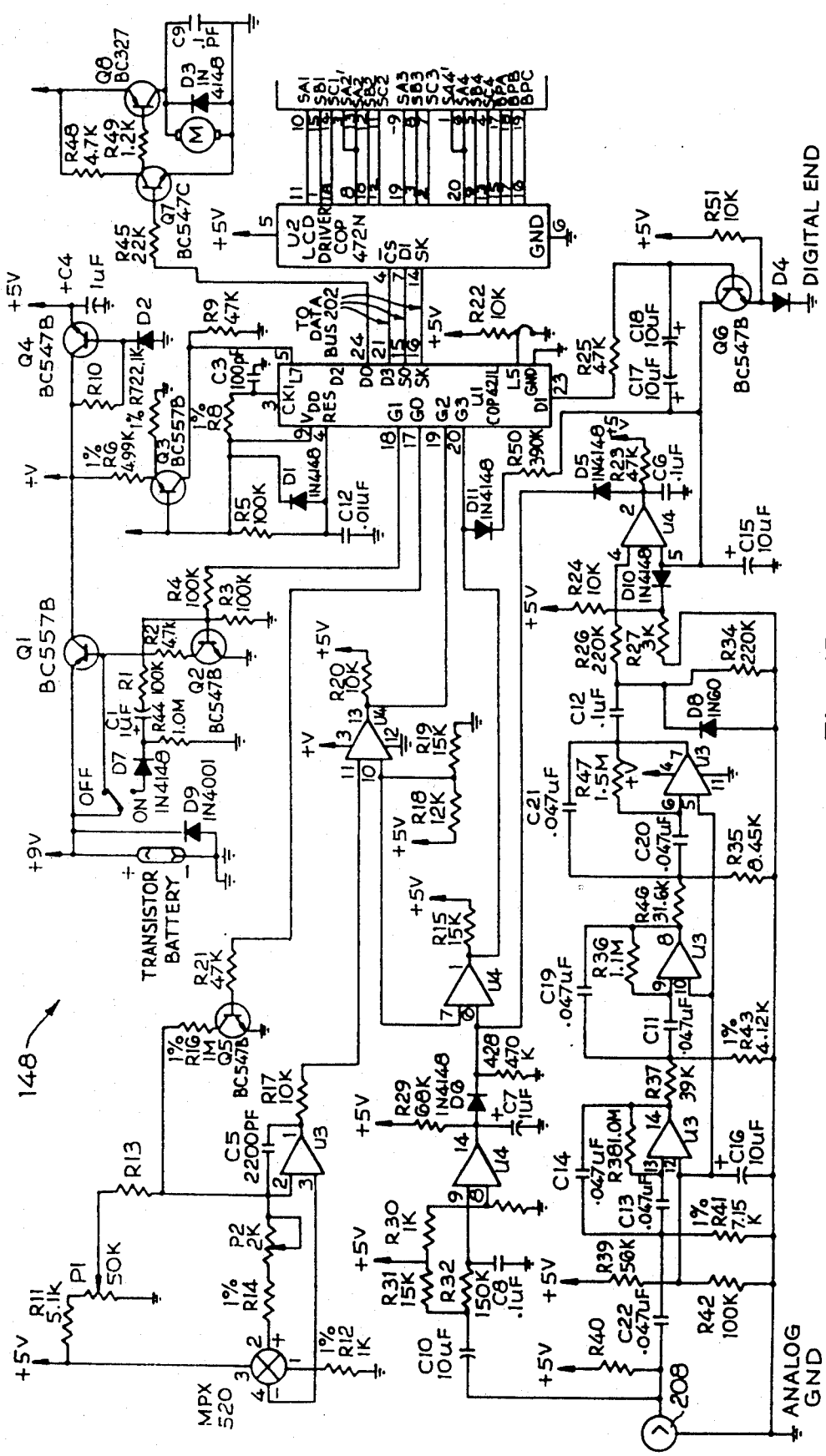
FIG. 13 is a detailed electronic schematic of a portion of the interface circuitry of the system of FIG. 4.

FIG. 13 is a detailed schematic diagram of the interface circuitry 148 between the cuff 106 and the data bus 202. Acoustic signals from the cuff 106 are detected in a condenser microphone 208. The condenser microphone 208 serves as the electrical input to the circuitry 148. Signals from the microphone 208 are processed in the circuitry of FIG. 13 and coupled to the data bus 202.

Figure 14A:
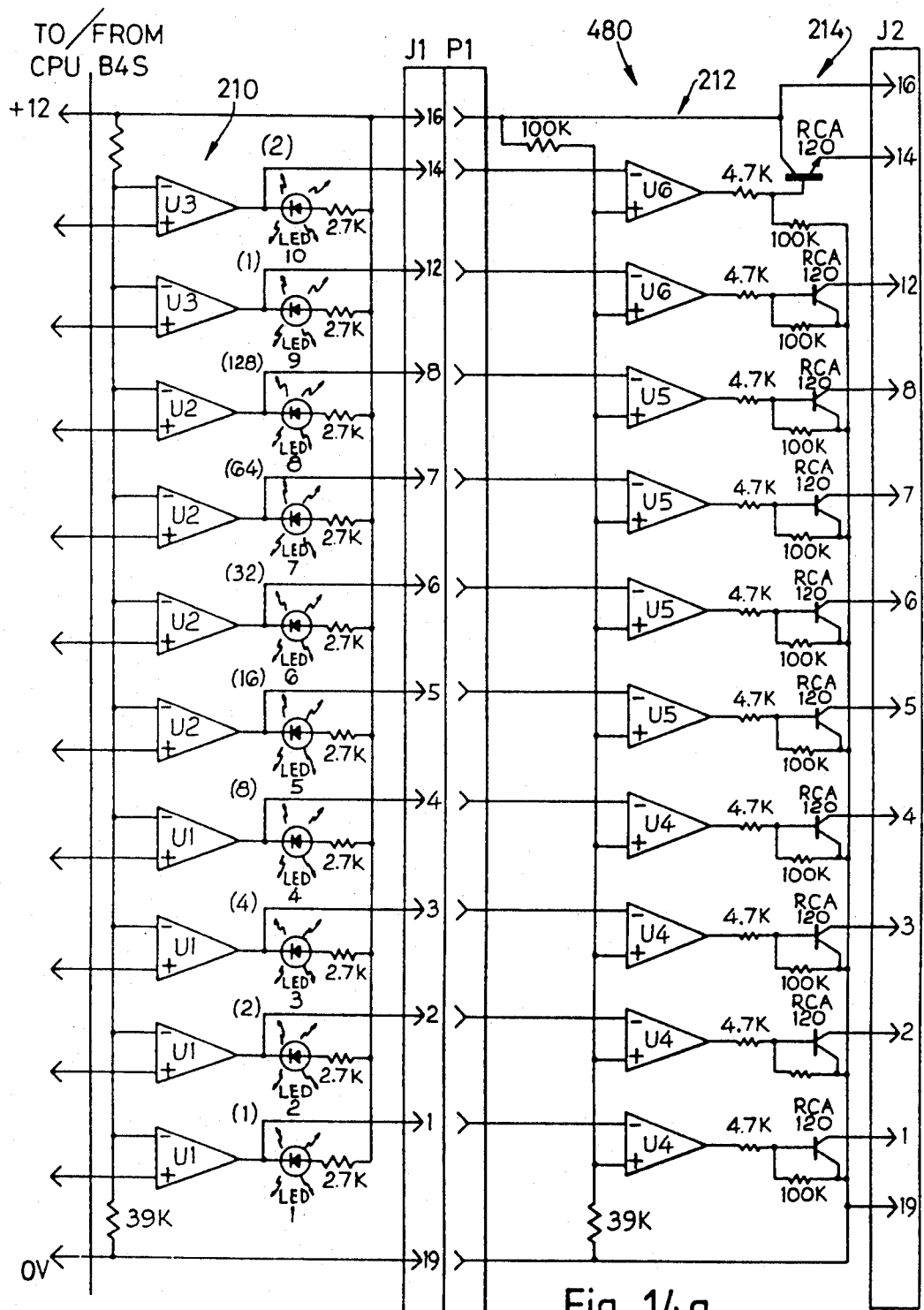
FIGS. 14a and 14b, taken together, are a detailed electronic schematic of another portion of the interface circuitry of the system of FIG. 4.
Figure 14B:
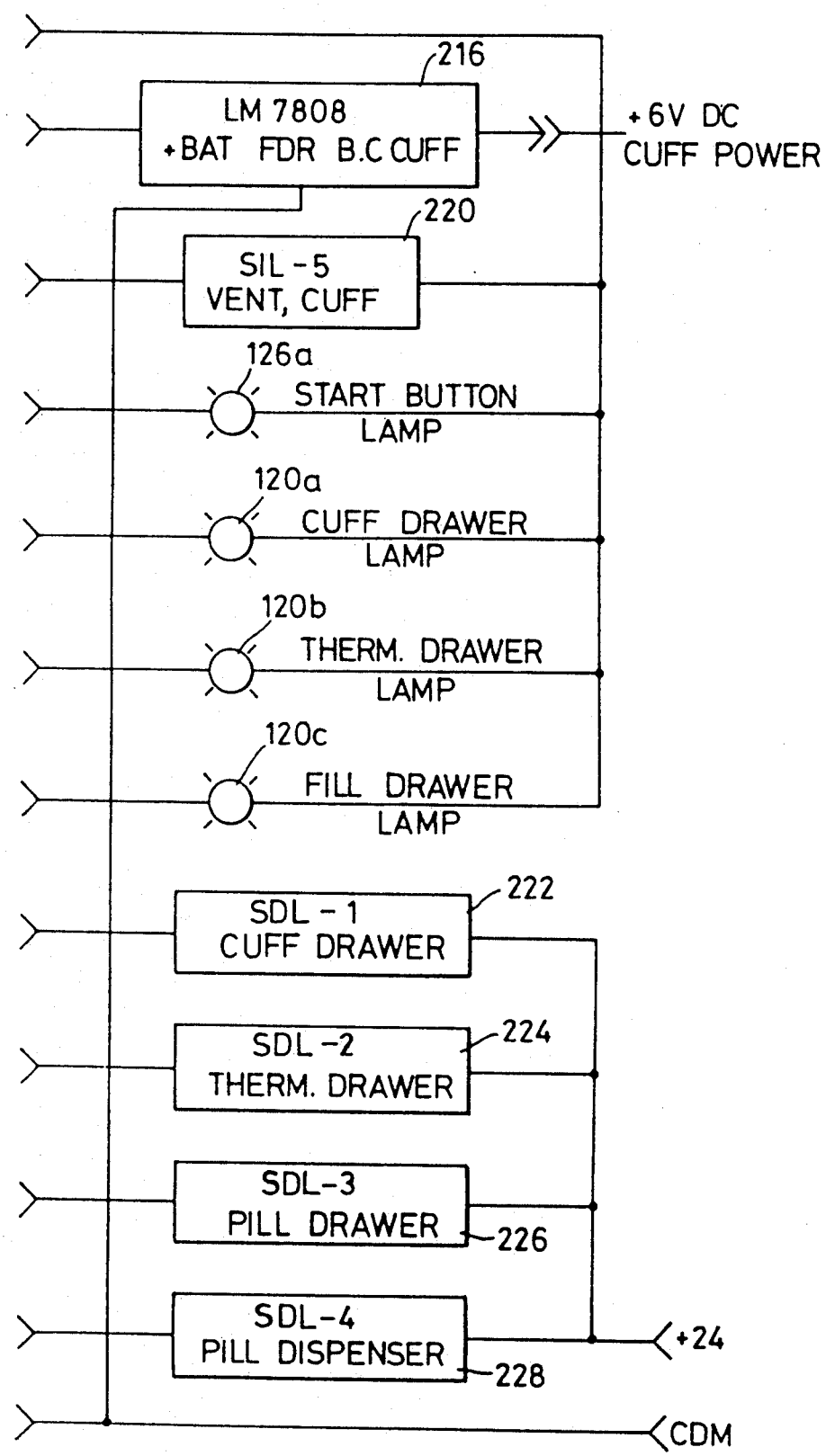

FIGS. 14A and 14B, taken together, are a detailed schematic of the driver circuitry 48a.

Elements U1, U2 and U3 are LM3302 type comparators. Elements U4, U5 and U6 are operational amplifiers type LM324. Signals from the address bus 200 and the data bus 202 are received at inputs to the plurality of comparators 210. Outputs from the comparators 210 provide inputs to a plurality of operational amplifiers 212

Outputs through the operational amplifiers 212, via a plurality of transistor drive circuits 214 provide electrical signals and power levels for an 8-volt regulated supply 216 to power the circuitry for the blood pressure cuff 106, and to illuminate indicators 120a, 120b, 120c and 126a. The drive transistors 214 also provide signals to actuate a cuff venting solenoid 220, a cuff drawer releasing solenoid 222; a thermometer drawer releasing solenoid 224; a dispensed product drawer releasing solenoid 226 and a product dispensing mechanism actuating solenoid 228.

The principles of the present invention, it will be understood, are applicable to computer based systems, with or without speech recognition, usable by persons of good health and sound body. Further, it will be understood that systems in accordance with the present invention can also be used in hospitals or nursing homes.

From the foregoing, it will be observed that numerous variations and modifications may be effected without departing from the spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

```
1  '*************************************************************
2  '*                                                             *
3  '*                                                             *
4  '*                         ADDENDUM                            *
5  '*                                                             *
6  '*                                                             *
7  '*                       MARCH 1988                            *
8  '*************************************************************
9  GOTO 560
10 ADC.SETUP=&H91B:ALTOUT12.B=&H738:ALTOUT12.BT=&H799:ALTOUT12.R=&H7FD
20 ALTOUT12.RT=&H860:ALTOUT12.S=&H6E5:ALTOUT12.ST=&H70D:ALTOUT8.B=&H2A9
30 ALTOUT8.BT=&H335:ALTOUT8.R=&H3C7:ALTOUT8.RT=&H459:ALTOUT8.S=&H220
40 ALTOUT8.ST=&H262:DAC.SETUP=&H1A:INADC12.B=&HD5E:INADC12.BT=&HDF1
50 INADC12.EXTCLOCK=&HE94:INADC12.S=&HCE5:INADC12.ST=&HD16:INADC8.B=&H9C3
60 INADC8.BT=&HA31:INADC8.EXTCLOCK=&HAA2:INADC8.S=&H93E:INADC8.ST=&H974
65 OUTDAC12.B=&H550:OUTDAC12.BT=&H5B5:OUTDAC12.R=&H61D:OUTDAC12.RT=&H676
67 OUTDAC12.S=&H4F1:OUTDAC12.ST=&H51F:OUTDAC8.B=&H92:OUTDAC8.BT=&HF3
68 OUTDAC8.R=&H157:OUTDAC8.RT=&H1BA:OUTDAC8.S=&H3F:OUTDAC8.ST=&H67
69 SCAN12.B=&HFFD:SCAN12.BT=&H1095:SCAN12.S=&HF43:SCAN12.ST=&HF97
70 SCAN8.B=&HBBD:SCAN8.BT=&HC4E:SCAN8.S=&HAFF:SCAN8.ST=&HB54
80 DEF SEG=0
85 CSEG=(256*PEEK(&H3CB))+PEEK(&H3CA)
90 DEF SEG=CSEG
91 '
92 '
93 '
```

```
94 '
95 '
96 '
97 '
98 '
99 '
100 '***************************************************************
210 ADDRESS%=&H300                          'module address
220 CALL ADC.SETUP(ADDRESS%)                'setup address
230 DIM ARRAY%(1000)
235 GOTO 560
236 'ANALOG BOARD SUB  ******************
240 BCHANNEL%=0                             'beginning channel
250 ECHANNEL%=4                             ' end channel
260 TIMING%=1000                            'around 5ms
270 LENGTH%=1                               '1 PASS SCAN
280 SCANNO%=ECHANNEL%-BCHANNEL%+1
290 CALL SCAN8.B(BCHANNEL%,ECHANNEL%,TIMING%,LENGTH%,ARRAY%(1))
300 '
310 PRINT "CHANNEL 0      CHANNEL 1      CHANNEL 2      CHANNEL 3      CHANNEL
320 PRINT
330 FOR I=1 TO LENGTH%*SCANNO% STEP SCANNO%
340 PRINT ARRAY%(I),ARRAY%(I+1),ARRAY%(I+2),ARRAY%(I+3),ARRAY%(I+4)
350 LET V=ARRAY%(I)
360 LET W=ARRAY%(I+1)
370 LET X=ARRAY%(I+2)
380 LET Y=ARRAY%(I+3)
390 LET Z=ARRAY%(I+4)
399 NEXT
400 RETURN    'END OF ANALOG SUB   *****************
410 '
420 '
500 'CHECK TIME ROUTINE
510 DT%=2    '**** **** **** **** **** **** **** **** **** ****
520 T%=VAL(MID$(TIME$,4,2))+DT%
530 IF T%=>60 THEN T%=T%-60
540 IF VAL(MID$(TIME$,4,2))=T% THEN 550 ELSE 540
545 GOTO 590
550 '
560 SRT%=INP(H301)        'PUSH BUTTON TO START
570 IF SRT%<=1 THEN GOTO 600 ELSE GOTO 560
580 '
590 'SETUP & DATA  **** **** **** **** **** **** **** **** ****
600 '
605 OUT &H30B,&H89    'WAKEUP 8255 AND CONFIG PORTS A&B OUT C IN/OUT
606 OUT &H309,&HF
610 COUNT=1000:COUNT2=3000:REPS=2:PRESSED%=1
620 HOSP=3663:MARY=3663:DOC=3663             '*****PHONE NUMBERS******
630 FLAG1=0:FLAG2=0:FLAG3=0:FLAG4=0:FLAG5=0:FLAG6=0:FLAG7=0:FLAG8=0
640 SYSLO=100:SYSHI=150:DILO=60:DIHI=90   'BLOOD PRESSURE LIMITS
650 PULSLO=60:PULSHI=110  'PULSE LIMITS
660 THIGH=100:TLOW=96.5  'TEMPERATURE LIMITS
670 PULS=80:BPS=90:BPD=60:TEMP=98.6   'TEST DATA
680 OPEN "TISPCH" FOR OUTPUT AS #1:PRINT #1,"RESET"
690 PRINT #1, "VOLUME=8"
700 PRINT #1, "LOAD=NAME"
709 PRINT #1, "RECOGNIZE=ON"
710 PRINT #1, "RECOGNIZE=NAME"
711 PRINT #1, "SPEAKFILE=WHO.MSG"
712 FOR L=1 TO COUNT: WHO$=INKEY$:IF WHO$<>"" THEN 713 ELSE NEXT L
713 IF WHO$="1" THEN PRINT #1, "LOAD=MIKE":PRINT #1, "RECOGNIZE=MIKE":HELLO$=
714 IF WHO$="2" THEN PRINT #1, "LOAD=TAM":PRINT #1, "RECOGNIZE=TAM":HELLO$="
715 IF WHO$="3" THEN PRINT #1, "LOAD=STEV":PRINT #1, "RECOGNIZE=STEV":HELLO$=
720 GOTO 711    ' NAME NOT RECOGNIZED
725 '**** **** **** **** **** **** **** **** **** **** **** ****
730 ' WAKEUP CALL
731 PRINT HELLO$
740 LOOP=0
750 FOR I=500 TO 1000 STEP 250:SOUND I,9:NEXT I
755 HOUR1=VAL(LEFT$(TIME$,2)) :MIN1=VAL(MID$(TIME$,4,2))
756 IF HOUR1>12 THEN HOUR1=HOUR1-12
760 PRINT #1, "SPEAKFILE=";HELLO$
```

```
770 PRINT #1, "SPEAKTEXT=";HOUR1;MIN1;" ."
780 FOR L=1 TO COUNT: ANS$=INKEY$:IF ANS$<>"" THEN 790 ELSE NEXT L
790 IF ANS$="Y" THEN 870
800 PRINT LOOP
810 IF LOOP>REPS THEN GOTO 820 ELSE 850   'PHONE HOSPITAL
820 FLAG1=1:WHO$="+":NUMB=HOSP:GOSUB 2000
830 'PRINT "PATIENT WON'T RESPOND..PHONE CALL MADE."
840 GOTO 1810
850 LOOP=LOOP+1:GOTO 750
860 ' PATIENT FEELINGS
870 LOOP=0
880 PRINT #1, "SPEAKFILE=FEEL.MSG"
890 FOR L=1 TO COUNT: FEEL$=INKEY$:IF FEEL$<>"" THEN 900 ELSE NEXT L
900 IF FEEL$="O" OR FEEL$="F" OR FEEL$="G" THEN 1010
910 IF FEEL$="B" OR FEEL$="A" OR FEEL$="T" THEN GOTO 940
920 IF LOOP>REPS THEN GOTO 1000 ELSE LOOP=LOOP+1
930 GOTO 880
940 ' NEGATIVE FEEL RESPONSE - CALL HOSPITAL AFTER TAKING VITALS?
950 PRINT #1, "SPEAKFILE=PHONE.MSG"
960 FOR L=1 TO COUNT: PHON$=INKEY$:IF PHON$<>"" THEN 970 ELSE NEXT L
970 IF PHON$="Y" THEN FLAG2=1 ELSE 1010   'SET PHONE FLAG
980 PRINT #1, "SPEAKFILE=VITALS.MSG"
990 GOTO 1010
1000 FEEL$="NO RESPONSE"   'NO FEELING RESPONSE
1010 FEEL$="NONE"      'RECORD FEELING & GO ON TO BP
1020 '
1030 ' BEGIN BP/PULSE PROMPT ROUTINE
1040 '
1050 PRINT #1, "SPEAKFILE=BP.MSG"
1051 OUT &H308,&H1    'OPENS BP DRAWER
1052 FOR A=1 TO 200 :NEXT A
1053 OUT &H308,&H30    ' TURN ON BP & START LITE
1060 PRINT #1, "SPEAKFILE=FINGER.MSG"
1061 A%=INP(&H30A) :IF A%<=PRESSED% THEN 1062 ELSE 1061
1062 PRINT "STARTING BP" :OUT &H309,&H2
1063 FOR B=1 TO 3: FOR D=1 TO 8000:NEXT D:NEXT B    ' 1 TO 6=1 MIN 45 SEC
1160 '
1170 '
1180 '
1190 OUT &H309,&H1 :GOSUB 4010       'VENT BP CUFF - BP SUB
1195 OUT &H309,&HF :OUT &H308,&H0    'TURN BP OFF
1200 PRINT #1, "SPEAKFILE=BPOFF.MSG"    'BP DONE
1201 FOR J=1 TO COUNT2 :NEXT J
1209 'PRINT #1, "SPEAKFILE=CLOSE.MSG"
1210 '
1220 ' TEMP PROMT ROUTINE
1230 '
1240 OUT &H308,&H2   ' OPEN THERM DRAWER
1241 FOR A=1 TO 200 :NEXT A
1242 OUT &H308,&H50     'TURN ON LITES
1250 PRINT #1, "SPEAKFILE=TEMP.MSG"
1260 TLOOP=0
1265 A%=INP(&H30A):IF A%<=PRESSED% THEN 1270 ELSE 1265
1266 PRINT "TEMP STARTED."
1270 FOR G=1 TO COUNT2:NEXT G    'WAIT 30 SEC
1280 ' MARKER
1380 GOSUB 3010   'CALL SUB TO TAKE TEMP.
1390 IF TLOOP=1 THEN GOTO 1260
1395 TLOOP=0
1400 PRINT #1, "SPEAKFILE=TEMPOFF.MSG"
1401 'FOR J=1 TO COUNT         'CHECK THAT DRAWER IS CLOSED
1402 'DOOR%=INP(H300)
1403 'IF DOOR%=PRESSED THEN GOTO 1440
1404 'NEXT J
1406 'IF TLOOP>REPS THEN GOTO 1409 ELSE TLOOP=TLOOP+1
1407 'GOTO 1400
1409 'PRINT #1, "SPEAKFILE=CLOSE.MSG"
1410 '
1420 ' DISPENSE PILLS ROUTINE
1430 '
1440 PRINT #1, "SPEAKFILE=MED.MSG"
1450 OUT &H308,&H8     'DROP PILL
```

```
1451 FOR A=1 TO 200 :NEXT A
1452 OUT &H308,&H0
1453 FOR A=1 TO 500 :NEXT A
1454 OUT &H308,&H4    'OPEN PILL DRAWER
1455 FOR A=1 TO 200 :NEXT A
1456 OUT &H308,&H80
1460 PRINT #1, "SPEAKFILE=PILLS.MSG"
1461 FOR I=1 TO COUNT:NEXT I
1462 PRINT #1, "SPEAKFILE=DIDPILL.MSG
1463 FOR L=1 TO COUNT:DID$=INKEY$:IF DID$="Y" THEN 1480 ELSE NEXT L
1464 PRINT #1, "SPEAKFILE=DIDPILL2.MSG"
1465 GOTO 1461
1480 OUT &H308,&H0    'LITES OFF
1490 ' PHONE CALL PROMPT ROUTINE
1500 '
1510 IF FLAG2=0 AND FLAG3=0 AND FLAG4=0 AND FLAG5=0 AND FLAG6=0 AND FLAG7=0 ;
1520 PRINT #1, "SPEAKFILE=CALLHOS.MSG"
1530 WHO$="+":NUMB=HOSP:GOSUB 2000
1540 GOTO 1730    'OFFER TO MAKE ANOTHER CALL
1550 LOOP=0
1560 PRINT #1, "SPEAKFILE=TALK.MSG"
1570 FOR L=1 TO COUNT:TALK$=INKEY$:IF TALK$<>"" THEN 1580 ELSE NEXT L
1580 IF TALK$="Y" THEN 1620    'PLACE PHONE CALL
1590 IF TALK$="N" THEN 1800    'GO ON
1600 IF LOOP>REPS THEN GOTO 1800 ELSE LOOP=LOOP+1
1610 GOTO 1560
1620 'SETUP PHONE CALL
1630 LOOP=0:NUMB=0
1640 PRINT #1, "SPEAKFILE=TALK2.MSG"
1650 FOR L=1 TO COUNT:WHO$=INKEY$:IF WHO$<>"" THEN 1660 ELSE NEXT L
1660 IF WHO$="+" THEN NUMB=HOSP
1670 IF WHO$="D" THEN NUMB=DOC   'DOCS PHONE NO.
1680 IF WHO$="M" THEN NUMB=MARY  'MARYS PHONE NO.
1690 IF NUMB>0 THEN GOTO 1720
1700 IF LOOP>REPS THEN 1730 ELSE LOOP=LOOP+1
1710 GOTO 1640
1720 GOSUB 2000
1730 LOOP=0
1740 PRINT #1, "SPEAKFILE=TALK3.MSG"
1750 FOR L=1 TO COUNT:ANOTH$=INKEY$:IF ANOTH$<>"" THEN 1760 ELSE NEXT L
1760 IF ANOTH$="Y" THEN GOTO 1620
1770 IF ANOTH$="N" THEN GOTO 1800
1780 IF LOOP>REPS THEN GOTO 1800 ELSE LOOP=LOOP+1
1790 GOTO 1740
1800 PRINT #1, "SPEAKFILE=QUIET.MSG"
1810 CLOSE #1:GOTO 560    ' LOOP AROUND AGAIN
1820 'END
1830 '
1840 '
1850 '
2000 'SUB TO PLACE PHONE CALL
2005 '
2010 GOTO 2900   'SKIP PHONE CALL
2020 OPEN "COM2:1200,N,8,1" AS #2
2030 PRINT #2, "ATDT";NUMB
2040 LOOP=0:A$=""
2050 B$=""
2060 B$=INPUT$(1,#2)
2070 IF (ASC(B$)<48) OR (ASC(B$)>122) THEN 2050 ELSE LOOP=LOOP+1
2080 IF LOOP<9 THEN 2050 ELSE A$=A$+B$
2090 IF A$<>"CONNECT" THEN 2050
2500 PRINT #2, CHR$(7), CHR$(7), CHR$(7)
2510 'PRINT #2, "STEVE NEEDS ATTENTION"
2520 PRINT #2, "H.A.N.C. NO. 33   LOCATION NO. 12"
2530 PRINT #2, "PHONE 111-555-1212"
2540 PRINT #2, "BP : ";BPS;"/";BPD
2550 PRINT #2, "PULSE : ";PULS
2560 PRINT #2, "TEMPERATURE : ";TEMP
2800 CLOSE #2
2900 RETURN
3000 '
3010 'TEMP ROUTINE
```

```
3020 '
3030 'GOSUB 240          ' CALL ANALOG ASSEMB ROUTINE
3040 'TEMP=Y             'GET TEMP FROM REG. Y
3050 T=FIX(TEMP):DEC=CINT(10*(TEMP-FIX(TEMP)))/10  'TRUNC/ROUND TO TENTHS
3060 T=T+DEC
3070 PRINT #1, "SPEAKTEXT=YOUR TEMPERATURE IS";T;"DEGREES."
3080 IF TEMP>TLOW AND TEMP<THIGH THEN PRINT #1, "SPEAKFILE=TEMPOK.MSG":TLOOP=
3090 IF TLOOP=1 THEN 3130
3100 IF TEMP<TLOW THEN PRINT #1, "SPEAKFILE=TEMPLOW.MSG"
3110 IF TEMP>THIGH THEN PRINT #1, "SPEAKFILE=TEMPHI.MSG"
3120 TLOOP=1:RETURN     'REPEAT TEMP MEASURE
3130 'TEMP STILL OUT OF RANGE
3140 TLOOP=0
3150 IF TEMP<TLOW THEN PRINT #1, "SPEAKFILE=TEMPLOW2.MSG":FLAG3=1:RETURN
3160 IF TEMP>THIGH THEN PRINT #1, "SPEAKFILE=TEMPHI2.MSG":FLAG4=1:RETURN
4000 '
4010 'BP/P ROUTINE
4020 '
4030 PLOOP=0
4040 'GOSUB 240         ' CALL ANALOG ASSEMB ROUTINE
4050 'PULS=X:BPS=V:BPD=W   'GET BLOOD PRESSURE AND PULSE FROM X,Y,W
4060 PRINT #1, "SPEAKTEXT=YOUR PULSE IS";PULS;" AND YOUR BLOOD PRESSURE IS";E
4070 IF PULS>PULSLO AND PULS<PULSHI THEN PRINT #1, "SPEAKFILE=PULSOK.MSG" ELS
4080 FLAG7=0:FLAG8=0:GOTO 4140
4090 IF PLOOP<>0 THEN 4130
4100 IF PULS<PULSLO THEN PRINT #1, "SPEAKFILE=PULSLO.MSG":FLAG7=1
4110 IF PULS>PULSHI THEN PRINT #1, "SPEAKFILE=PULSHI.MSG":FLAG8=1
4120 PLOOP=PLOOP+1:GOTO 4050   'REPEAT PULSE/BP
4130 'STILL OUT OF RANGE  GO ON TO BP
4140 'GO ON TO BP
4150 IF (BPS>SYSLO AND BPS<SYSHI) AND (BPD>DILO AND BPD<DIHI) THEN PRINT #1,
4160 IF BPS<SYSLO OR BPD<DILO THEN PRINT #1, "SPEAKFILE=BPLO.MSG" ELSE 4180
4170 FLAG5=1:RETURN
4180 'BP SHOULD BE HIGH
4190 PRINT #1, "SPEAKFILE=BPHI.MSG"
4200 FLAG6=1:RETURN
```

What is claimed is:

1. An interactive patient assistance device comprising:

a housing, a prescribed dosage of medication, a prescribed physical testing device providing an output indicative of a physical health parameter of the patient, including means within the housing and attached to the physical testing device for reading the output of the physical testing device, first storage means within the housing for storing the prescribed dosage of medication within the housing away from access by the patient, second storage means within the housing for storing the prescribed testing device within the housing away from access by the patient, first and second delivery means associated, respectively, with each the first and second storage means for selectively making the prescribed dosage of medication available to the patient in response to a first command signal and for selectively making the prescribed testing device available for use by the patient in response to a second command signal, patient command means for receiving a interpreting prescribed commands made by the patient, first memory means for storing a first prescribed schedule for delivery the prescribed dosage of medication, second memory means for storing a second prescribed schedule for delivering the prescribed testing device, first control means for issuing the first command signal to actuate the first delivery means for making the prescribed dosage of medication available to the patient in response to either the prescribed schedule stored in the first memory means or the receipt of a prescribed command by the patient command means, and second control means for issuing the second command signal to actuate the second delivery means for making the prescribed testing device available to the patient in response to either the prescribed schedule stored in the second memory means or the receipt of a prescribed command by the patient command means.

2. A device according to claim 1 and wherein the patient command means includes speech recognition means for receiving and interpreting prescribed verbal commands made by the patient.

3. A device according to claim 1 and wherein at least one of the first and second delivery means includes a drawer movable between a closed position within the housing and an opened position outside the housing, and wherein the associated one of the control means moves the drawer from its closed to its opened position.

4. A device according to claim 3 and wherein the at least one delivery means includes means for biasing the drawer toward its opened position and releasable locking for retaining the drawer in its closed position against the force of the biasing means, and wherein the associated one of the control means releases the locking means.

5. A device according to claim 1
wherein the first storage means includes means for storing multiple dosages of medication,
wherein the first delivery means includes a drawer movable between a closed position within the housing and an opened position outside the housing, and
wherein the first control means delivers a medication dose from the first storage means into the drawer when it is in its closed position and moves the drawer from its closed to its opened position.

6. A device according to claim 1
and further including third control means connected with the patient command means for altering a selected one of the prescribed schedules stored in the first and second memory means in response to a prescribed command made by the patient.

* * * * *

UNITED STATES PATENT AND TRADEMARK OFFICE
CERTIFICATE OF CORRECTION

PATENT NO. : 5,142,484
DATED : August 25, 1992
INVENTOR(S) : S. Kaufman et al

It is certified that error appears in the above-indentified patent and that said Letters Patent is hereby corrected as shown below:

Column 17, Claim 1, Line 60:
  Delete "a" and substitute -- and --

Column 17, Claim 1, Line 63:
  Delete "delivery" and substitute -- delivering --

Signed and Sealed this

Tenth Day of January, 1995

Attest:

BRUCE LEHMAN

Attesting Officer       Commissioner of Patents and Trademarks